(12) United States Patent
Shimada et al.

(10) Patent No.: US 6,489,331 B1
(45) Date of Patent: Dec. 3, 2002

(54) REMEDIES FOR DIABETES

(75) Inventors: Junichi Shimada, Shizuoka (JP); Yoshihisa Ohta, Kanagawa (JP); Kotaro Takasaki, Shizuoka (JP); Miho Suda, Shizuoka (JP); Hideaki Kusaka, Shizuoka (JP); Hiroshi Yano, London (GB); Satoshi Nakanishi, Kanagawa (JP); Yuzuru Matsuda, Tokyo (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 0 days.

(21) Appl. No.: 09/719,570
(22) PCT Filed: Jul. 2, 1999
(86) PCT No.: PCT/JP99/03583
§ 371 (c)(1),
(2), (4) Date: Apr. 9, 2001
(87) PCT Pub. No.: WO00/01388
PCT Pub. Date: Jan. 13, 2000

(30) Foreign Application Priority Data

Jul. 2, 1998 (JP) .............................................. 10-187705

(51) Int. Cl.$^7$ ........................ A61K 31/52; A61K 31/505
(52) U.S. Cl. ........................ 514/262; 514/267; 514/866
(58) Field of Search .............................. 514/183, 220, 514/267, 866, 262

(56) References Cited

U.S. PATENT DOCUMENTS 5,270,316 A * 12/1993 Suzuki et al. ................ 514/267
5,747,472 A *  5/1998 Krenitsky et al. ............. 514/45
6,306,847 B1 * 10/2001 Tsumuki et al. ............. 514/183

FOREIGN PATENT DOCUMENTS

| EP | 0423805 | 4/1991 |
| EP | 0884318 | 12/1998 |
| JP | 3204880 | 9/1991 |
| JP | 10158267 | 6/1998 |
| WO | 98/15555 | 4/1998 |

OTHER PUBLICATIONS

English Language Abstract of JP 10–158267.
Fumio Fumio Suzuki et al., "Communication to the Editor: 7,8–Dihydro–8–ethyl–2–(3–noradamatyl)–4–propyl–1H–imidazo[2,1–i]purin–5(4H–one: A Potent and WaterSoluble Adenosine A$_1$ Antagonist", J. Med. Chem., vol. 35, pp. 3578–3581, (1992).
Fumio Suzuki et al., "Adenosine A1 Antagonists. 3. Structure–Activity Relationships on Amelioration against Scopolamine–or N6–((R)–Phenylisopropyl)adenosine–Induced Cognitive Disturbance", J. Med. Chem., vol. 36, pp. 2508–2518 (1993).
.D.L. Temple, Jr. et al., "Substituted 6,7–Dihydroimidazo[1, 2–a]purin–9(4H)–ones", J. Med. Chem., vol. 23, pp. 1188–1198 (1980).
Hiroyuki Sawanishi et al., "Selective Inhibitors of Cyclic AMP–Specific Phosphodiesterase: Heterocycle–Condensed Purines", J. Med. Chem., vol. 40, pp. 3248–3253 (1997).
Junichi Shimada et al., "A Convenient Sythesis of Tricyclic Purine Derivatives", J. Heterocyclic. Chem., vol. 30, pp. 241–246 (1993).
Scherer S. Duke et al., "Synthesis and Biological Evaluation of Sparsomycin Analogues", J. Med. Chem., vol. 26, pp. 1556–1561 (1983).
Hideo Seki et al., "Studies on Optically Active Active Amino Acids. V. Synthesis of Optically Active α–Aminoalcohols by the Reduction of α–Amino Acid Esters with Esters with Sodium Borohydride.", Chem. Pharm. Bull., vol. 13, pp. 995–1000 (1965).
Jerome M. Feldman, M.D., "Evaluations of New Drugs: Glyburide: A Second–generation Sulfonylurea Hypoglycemic Agent: History, Chemistry, Metabolism, Pharmacokinetics, Clinical Use and Adverse Effects", Pharmacotherapy, vol. 5, No. 2, pp. 43–62 (1985).
Kinori Kosaka et al., "Phase III– Study of a Novel Hypoglycemic Agent, AY4166, on NIDDM Patients in Japan (1): a–Glucosidase Inhibitor, Voglibose–Controlled Multicenter Double Blind Study", Clinical Pharmacology and Therapy, vol. 7, No. 5, pp. 121–149 (1997).
Hideki Ohnota et al., "Novel Rapid– and Short–Acting Hypoglycemic Agent, a Calcium(2s)–2–benzyl–3–(cis–hexahydro–2–isoindolinylcarbonyl) Propionate (KAD–1229) That Acts on the Sulfonylurea Receptor: Comparison on Effect Between KAD–1229 and Gliclazide", Journal of Pharmacology and Experimental Therapeutics, vol. 269, No. 2, pp. 489–495 (1994).

* cited by examiner

Primary Examiner—Kevin E. Weddington
(74) Attorney, Agent, or Firm—Greenblum & Bernstein, P.L.C.

(57) ABSTRACT

A medicament for the therapeutic treatment of diabetes which comprises as an active ingredient a compound represented by the general formula (I):

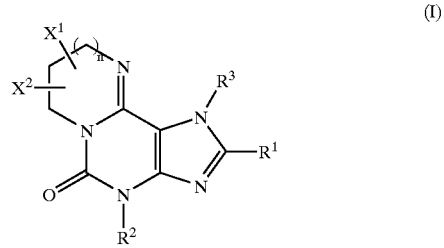

(I)

wherein $R^1$ represents a hydrogen atom, a lower alkyl group, a substituted or unsubstituted aryl group, or a substituted or unsubstituted aromatic heterocyclic group, $R^2$ represents a hydrogen atom, a lower alkyl group, a substituted or unsubstituted aralkyl group, a substituted or unsubstituted aryl group, or a substituted or unsubstituted aromatic heterocyclic group, $R^3$ represents a hydrogen atom, a lower alkyl group or a substituted or unsubstituted aralkyl group, $X^1$ and $X^2$ independently represent a hydrogen atom, a lower alkyl group, a substituted or unsubstituted aralkyl group, or a substituted or unsubstituted aryl group, and the symbol "n" represents an integer of from 0 to 3, or a physiologically acceptable salt thereof.

16 Claims, No Drawings

REMEDIES FOR DIABETES

TECHNICAL FIELD

The present invention relates to an enhancer of insulin secretion and a medicament for the treatment of diabetes, which comprise a condensed purine derivative as an active ingredient.

BACKGROUND ART

Diabetes is a metabolic abnormality mainly of glycometabolism, resulting from insufficient insulin secretion, decreased sensitivity of target cells of insulin and so forth, and principally characterized by noticeable hyperglycemia. If the hyperglycemia continues for a long period of time, serious complications arise in various organs and nerves such as retinopathy, nephropathy and neuropathy, which are caused mainly by vascular lesion. Therefore, for the treatment of diabetes, it is extremely important to control and maintain blood glucose level at a normal level, and methods for that purpose have been studied since old days.

For a type of diabetes where onset is gradual and insulin therapy is not necessarily required for life support (non-insulin dependent diabetes: NIDDM), blood glucose level can be controlled by combination of exercise therapy and drug therapy. As the drugs, insulin secretion enhancers, one of orally available hypoglycemic agents, have widely been used clinically. However, since currently available insulin secretion enhancers all promote insulin secretion non-dependently on glucose level, they cause problems of severe hypoglycemia or insufficient control of blood glucose if doses are not appropriate, and are not fully satisfactory drugs. If a hypoglycemic agent can be provided that is capable of enhancing insulin secretion dependently on a blood glucose level, the agent is expected to be extremely useful for blood glucose control of patients suffering from diabetes because the risk of hypoglycemia due to an excess dosage can be avoided.

As purine derivatives, the compounds of the following formula (I) having diuretic action, antiasthmatic action, anti-dementia action, bronchodilatation action, antiallergic action, antiulcer action and so forth are known (Japanese Patent Unexamined Publication (Kokai) No.3-204880/1991; Journal of Medicinal Chemistry, vol. 35, p.3578, 1992; Journal of Medicinal Chemistry, vol. 36, p.2508, 1993; International Publication WO98/15555). Journal of Medicinal Chemistry, vol. 23, p.1188, 1980 discloses that the compounds represented by the formula (A) have bronchodilatation action. Furthermore, Journal of Medicinal Chemistry, vol. 40, p.3248, 1997 discloses that the compounds represented by the formula (B) have inhibitory action against type IV phosphodiesterase (bronchodilatation action).

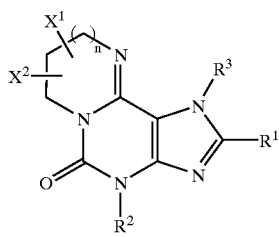

(I)

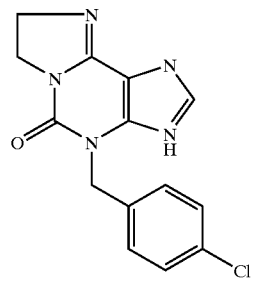

(A)

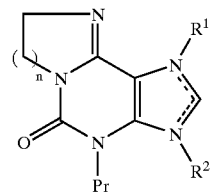

(B)

DISCLOSURE OF THE INVENTION

An object of the present invention is to provide a medicament useful for the therapeutic treatment of diabetes and the prophylactic and/or therapeutic treatment of complications of diabetes. More specifically, the object of the present invention is to provide a medicament having action of enhancing insulin secretion in a blood glucose level-dependent manner.

The inventors of the present invention conducted various studies to achieve the foregoing object. As a result, we found that the compounds represented by the following general formula (I) have insulin secretion enhancing action, and that the compounds are useful as an active ingredient of a medicament for the treatment of diabetes. The present invention was achieved on the basis of these findings.

The present invention thus provides medicaments for the therapeutic treatment of diabetes which comprise compound represented by the general formula (I) or a physiologically acceptable salt thereof as an active ingredient:

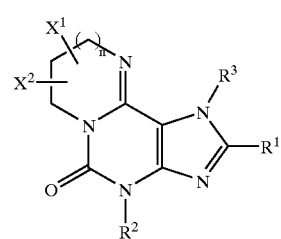

(I)

wherein $R^1$ represents a hydrogen atom, a lower alkyl group, a substituted or unsubstituted aryl group, or a substituted or unsubstituted aromatic heterocyclic group; $R^2$ represents a hydrogen atom, a lower alkyl group, a substituted or unsubstituted aralkyl group, a substituted or unsubstituted aryl group, or a substituted or unsubstituted aromatic heterocyclic group; $R^3$ represents a hydrogen atom, a lower alkyl group, or a substituted or unsubstituted aralkyl group; $X^1$ and $X^2$ independently represent a hydrogen atom, a lower alkyl group, a substituted or unsubstituted aralkyl group, or a substituted or unsubstituted aryl group; and n represents an integer of from 0 to 3. The invention also provides medicaments for the prophylactic and/or therapeutic treatment of a complication of diabetes which comprise the aforementioned compound or a physiologically acceptable salt thereof as an active ingredient.

According to other aspects of the present invention, there are provided hypoglycemic agents comprising a compound represented by the aforementioned formula (I) or a physiologically acceptable salt thereof as an active ingredient, and insulin secretion enhancers comprising a compound represented by the aforementioned formula (I) or a physiologically acceptable salt thereof as an active ingredient. These medicaments are preferably provided in the form of a pharmaceutical composition which comprises a compound represented by the aforementioned formula (I) or a physiologically acceptable salt thereof and one or more of pharmaceutical additives.

According to other aspects of the present invention, there are provided use of a compound represented by the aforementioned formula (I) or a physiologically acceptable salt thereof for the manufacture of the aforementioned medicaments; a method for the therapeutic treatment of diabetes which comprises the step of administering a therapeutically effective amount of a compound represented by the aforementioned formula (I) or a physiologically acceptable salt thereof to a mammal including human; a method for enhancing insulin secretion which comprises the step of administering a therapeutically effective amount of a compound represented by the aforementioned formula (I) or a physiologically acceptable salt thereof to a mammal including human; and a method for decreasing blood glucose level which comprises the step of administering a therapeutically effective amount of a compound represented by the aforementioned formula (I) or a physiologically acceptable salt thereof to a mammal including human.

The compounds represented by the general formula (I) will be hereinafter referred to as Compound (I).

Meanings of terms used herein are as follows. As the lower alkyl group or a lower alkyl moiety of a functional group containing the lower alkyl moiety (for example, an aralkyl group), an alkyl group having about 1 to 10 carbon atoms can be used, and the term "alkyl group" includes linear, branched and cyclic alkyl groups as well as those consisting of a combination thereof. A cyclic alkyl group or a cyclic alkyl moiety of an alkyl group may have one or more rings, and may have, for example, a bicyclic ring or tricyclic ring system.

Examples of the linear or branched lower alkyl group include a methyl group, an ethyl group, a n-propyl group, an isopropyl group, a n-butyl group, an isobutyl group, a sec-butyl group, a tert-butyl group, a n-pentyl group, a neopentyl group, a n-hexyl group, a n-heptyl group, a n-octyl group, a n-nonyl group and so forth. Examples of the cyclic lower alkyl group include a cyclopropyl group, a cyclobutyl group, a cyclopentyl group, a cyclohexyl group, a cycloheptyl group, a cyclooctyl group, a noradamantyl group, an adamantyl group and so forth.

Preferred examples of the lower alkyl group represented by $R^1$ include a linear or branched lower alkyl group (for example, a tert-butyl group, etc.), a monocyclic to tricyclic lower cycloalkyl group (for example, a cyclopropyl group, a cyclobutyl group, a cyclopentyl group, a cyclohexyl group, a 3-noradamantyl group, etc.) and a lower alkyl group substituted with a lower cycloalkyl group (for example, a cyclopropylmethyl group, a cyclopentylmethyl group, etc.). Among them, a 3-noradamantyl group and a cyclopentyl group are more preferred. As the lower alkyl group represented by $R^2$, a linear or branched lower alkyl group (for example, a methyl group, an ethyl group, a n-propyl group, etc.), a monocyclic lower cycloalkyl group or a lower alkyl group substituted with a lower cycloalkyl group (for example, a cyclopropylmethyl group etc.) is preferred. Among them, a n-propyl group is more preferred. As the lower alkyl group represented by $R^3$, a linear or branched lower alkyl group (for example, a methyl group, an ethyl group, etc.) is preferred, and a methyl group is more preferred. As the lower alkyl group represented by $X^1$ or $X^2$, a linear or branched lower alkyl group (for example, an ethyl group, an isopropyl group, a n-butyl group, an isobutyl group, a tert-butyl group, etc.), a monocyclic lower cycloalkyl group, or a lower alkyl group substituted with a lower cycloalkyl group (for example, a cyclohexylmethyl group etc.) is preferred. Among them, an ethyl group, an isopropyl group, an isobutyl group, and a tert-butyl group are more preferred.

As the aryl group or an aryl moiety of a functional group containing the aryl moiety (for example, an aralkyl group), an aromatic group consisting of a single ring or two or more condensed rings can be used. More specifically, an aryl group having 6 to 14 ring-membered carbon atoms is preferred. For example, a phenyl group, a naphthyl group, an indenyl group, an anthranyl group or the like may preferably be used. As the aralkyl group, for example, an aralkyl group having 7 to 15 carbon atoms can be used. More specifically, a benzyl group, a phenethyl group, a diphenylmethyl group, a naphthylmethyl group or the like may be used.

As the aromatic heterocyclic group, an aromatic heterocyclic group consisting of a single ring or two or more condensed rings can be used. The kind and number of hetero atom(s) contained in the aromatic heterocyclic group are not particularly limited. For example, one or more hetero atoms selected from the group consisting of a nitrogen atom, a sulfur atom, and an oxygen atom may be contained. More specifically, an aromatic heterocyclic group containing about 6 to 14 ring-membered carbon atoms is preferred. For example, a furyl group, a thienyl group, a pyrrolyl group, an imidazolyl group, a pyrazolyl group, a triazolyl group, a tetrazolyl group, an oxazolyl group, a thiazolyl group, a pyridyl group, a pyrazinyl group, a pyrimidinyl group, a pyridazinyl group, a triazinyl group, an indolyl group, an indazolyl group, a benzimidazolyl group, a benzoxazolyl group, a benzothiazolyl group, a quinolyl group, an isoquinolyl group, a phthalazinyl group, a naphthylidinyl group, a quinoxalinyl group, a quinazolinyl group, a cinnolinyl group, a purinyl group or the like may preferably be used.

When the aryl ring (including the aryl ring of an aralkyl group) or the aromatic heterocyclic ring has substituent(s), the kind, number and substitution position of the substituent (s) are not particularly limited. When two or more substituents exist, they may be the same or different. For example, the rings may have about 1 to 3 substituents. Examples of the substituents on the aryl ring or the aromatic heterocyclic ring include a substituted or unsubstituted lower alkyl group, a substituted or unsubstituted lower alkenyl group, a substituted or unsubstituted lower alkynyl group, a substituted or unsubstituted aralkyl group, a substituted or unsubstituted aryl group, a hydroxyl group, a substituted or unsubstituted lower alkoxy group, a substituted or unsubstituted aralkyloxy group, a substituted or unsubstituted aryloxy group, a substituted or unsubstituted aroyl group, a lower alkoxycarbonyl group, a substituted or unsubstituted lower alkylthio group, a substituted or unsubstituted lower alkylsulfonyl group, a carboxyl group, a substituted or unsubstituted carbamoyl group, a substituted or unsubstituted lower alkanoyl group, a halogen atom (the "halogen atom" used in the present specification may be any of a fluorine atom, a chlorine atom, a bromine atom, and an iodine atom), a nitro group, an amino group, a mono- or di(lower alkyl)-substituted amino group, a cyano group, a methylenedioxy group, an ethylenedioxy group and the like.

In the aforementioned functional groups, the above-explained groups may be used as the lower alkyl or a lower alkyl moiety of the functional groups containing a lower alkyl moiety (for example, the aralkyl group, the lower alkoxy group, the aralkyloxy group, the lower alkoxycarbonyl group, the lower alkylthio group, the lower alkylsulfonyl group, the lower alkanoyl group, the mono- or di(lower alkyl)-substituted amino group and the like). When the lower alkyl group or the lower alkyl moiety has substituent (s), the kind, number, and substitution position of the substituent(s) are not particularly limited. When two or more substituents exist, they may be the same or different. For example, the lower alkyl group or the lower alkyl moiety may have about 1 to 3 substituents. Examples of such substituents include a hydroxyl group, a halogen atom, a carboxyl group, a sulfo group, a phosphono group, ester groups derived from these acidic groups (a lower alkyl ester, an aralkyl ester, an aryl ester, etc.) and the like. More specific examples of the substituted alkyl group include a hydroxyethyl group, a trifluoromethyl group and the like. The two lower alkyl groups in the di(lower alkyl)-substituted amino group may be the same or different.

In the aforementioned functional groups, the aralkyl group or an aralkyl moiety of the aralkyloxy group has the same meaning as the aforementioned aralkyl group, and the aryl moiety of the aryl group, the aryloxy group, or the aroyl group has the same meaning as the aforementioned aryl group. As the lower alkenyl group, a linear or branched alkenyl group having 2 to 6 carbon atoms can be used. For example, a vinyl group, an allyl group, a 1-propenyl group, a methacryl group, a butenyl group, a crotyl group, a pentenyl group, a hexenyl group or the like may be used. As the lower alkynyl group, a linear or branched alkynyl group having 2 to 6 carbon atoms can be used. For example, an ethynyl group, a propynyl group, a butynyl group, a pentynyl group, a hexynyl group or the like may be used. The number of unsaturated bond in the alkenyl group or the alkynyl group is not particularly limited, and the number may preferably be 1.

When the aforementioned lower alkenyl group, lower alkynyl group, aralkyl group, aryl group, aralkyloxy group, aryloxy group, or aroyl group has substituent(s), the kind, number, and substitution position of the substituent(s) are not particularly limited. When two or more substituents exist, they may be the same or different. For example, the lower alkenyl group, lower alkynyl group, aralkyl group, aryl group, aralkyloxy group, aryloxy group, or aroyl group may have about 1 to 3 substituents. As the substituents, those exemplified as the substituents of the lower alkyl group may be used.

As the aryl group represented by $R^1$, a phenyl group, a 4-bromophenyl group and the like are preferred. As the aromatic heterocyclic group represented by $R^1$, a furyl group, a thienyl group and the like are preferred. As the aryl group represented by $R^2$, a phenyl group is preferred. As the aralkyl group represented by $R^2$, a benzyl group is preferred. As the aralkyl group represented by $R^3$, a benzyl group is preferred. As the aralkyl group represented by $X^1$ or $X^2$, a phenyl group is preferred. Examples of the aralkyl group represented by $X^1$ or $X^2$ include a benzyl group, a halogenated benzyl group (a 4-fluorobenzyl group, a 3-fluorobenzyl group, a 2-fluorobenzyl group, a 2,3-difluorobenzyl group, a 2,5-difluorobenzyl group, a 4-chlorobenzyl group, a 3-chlorobenzyl group, a 2,5-dichlorobenzyl group, a 4-bromobenzyl group, a 3-bromobenzyl group, an 3-iodobenzyl group, etc.), a 4-tert-butylbenzyl group, a 2-phenylbenzyl group, a 3-trifluoromethylbenzyl group, a 3-trifluoromethoxybenzyl group, a 3,5-bis(trifluoromethyl)benzyl group, a 4-hydroxybenzyl group, a 4-methoxybenzyl group, a 4-nitrobenzyl group, a 3-cyanobenzyl group, a 3-carboxybenzyl group, a 3-phenoxybenzyl group, a 3-(2-fluorophenoxy)benzyl group, a 4-benzyloxybenzyl group, a diphenylmethyl group, a phenethyl group, an α,α-dimethylbenzyl group and the like. When $X^1$ is a group other than a hydrogen atom, $X^2$ is preferably a hydrogen atom. A combination of a lower alkyl group as $X^1$ (for example, a methyl group) and an aralkyl group as $X^2$ (for example, a benzyl group) is also preferred.

In the aforementioned general formula (I), the substitution positions of $X^1$ and $X^2$ are not particularly limited, and they may substitute at any positions on the ring. When $X^1$ or $X^2$ is a substituent other than a hydrogen atom, the absolute configuration of the carbon atom to which it binds may be in either a S- or R-configuration. The symbol "n" may preferably be 0.

As the active ingredient of the medicament of the present invention, physiologically acceptable salts of Compound (I) may be used. Such physiologically acceptable salts include acid addition salts such as inorganic acid salts and organic acid salts; base addition salts such as metal salts, ammonium salts and organic amine addition salts; amino acid addition salts and the like. Examples of the physiologically acceptable acid addition salts include inorganic acid salts such as hydrochlorides, sulphates and phosphates, and organic acid salts such as acetates, maleates, fumarates, tartrates, and citrates. Examples of the physiologically acceptable metal salts include alkali metal salts such as sodium salts and potassium salts, alkaline earth metal salts such as magnesium salts and calcium salts, as well as aluminum salts, zinc salts and the like. Examples of the physiologically acceptable organic amine addition salts include addition salts of organic amines such as morpholine, piperidine and the like. Examples of the physiologically acceptable amino acid addition salts include addition salts of lysine, glycine, phenylalanine and the like.

As the active ingredient of the medicament of the present invention, the aforementioned compounds in free forms or physiologically acceptable salts thereof, as well as any hydrates and solvates thereof may be used. The kind of solvents forming the solvates is not particularly limited so long as they are physiologically acceptable. For example, ethanol, acetone and the like may be used. The compounds represented by the formula (I) may have one or more asymmetric carbons. As the active ingredient of the medicament of the present invention, any substances falling within the scope of the general formula (I) may be used, including optical isomers or diastereoisomers in pure forms, any mixtures of isomers, racemates and the like. When the compounds represented by the general formula (I) contain one or more double bonds, each configuration thereof may be in either a Z- or E-configuration.

The methods for the preparation of typical compounds falling within the compounds represented by the formula (I) are specifically disclosed in International Publication WO98/15555, and are also explained in Japanese Patent Unexamined Publication No. 3-204880/1991; Journal of Medicinal Chemistry, vol. 35, p.3578, 1992; Journal of Medicinal Chemistry, vol. 36, p.2508, 1993; Journal of Heterocyclic Chemistry, vol. 30, p.241, 1993 and the like. Furthermore, the methods for preparing preferred compounds shown below will be specifically explained in detail in the examples of the present specification. Therefore, those skilled in the art can prepare any compounds falling within the scope of the general formula (I) according to the processes disclosed in the aforementioned references or the manufacturing processes specifically described in the present specification, or by suitably changing regents and starting materials, and further by appropriately modifying or altering these processes, if necessary.

The intermediate compounds and target compounds obtained in these manufacturing processes can be isolated and purified by methods for purification conventionally used in the field of synthetic organic chemistry, for example, neutralization, filtration, extraction, washing, drying, concentration, recrystallization, various kinds of chromatography and the like. The intermediate compounds can also be used in subsequent reactions without particular purification. When salts of the compounds represented by the general formula (I) are prepared, the compounds in a free form may be dissolved or suspended in a suitable solvent, and a suitable acid or base is added to the mixture to form a salt, and then the resulting salts may be isolated and purified as required. It is also possible to convert a target substance obtained in a form of salt into a free form, and their converted into a desired salt.

Preferred examples of the active ingredient of the medicament of the present invention include:

(1) those wherein $R^1$ represents a hydrogen atom, a lower alkyl group, a substituted or unsubstituted aryl group, or a substituted or unsubstituted aromatic heterocyclic group, $R^2$ represents a lower alkyl group, a substituted or unsubstituted aralkyl group or a substituted or unsubstituted aryl group, $R^3$ represents a hydrogen atom, a lower alkyl group, or a substituted or unsubstituted aralkyl group, $X^1$ and $X^2$ independently represent a hydrogen atom, a lower alkyl group, a substituted or unsubstituted aralkyl group or a substituted or unsubstituted aryl group, and the symbol "n" represents 0, or physiologically acceptable salts thereof; more preferred examples include:

(2) those wherein $R^1$ represents a lower alkyl group, a substituted or unsubstituted aryl group, or a substituted or unsubstituted aromatic heterocyclic group, $R^2$ represents a lower alkyl group or a substituted or unsubstituted aryl group, $R^3$ represents a hydrogen atom or a substituted or unsubstituted aralkyl group, $X^1$ represents a hydrogen atom, a lower alkyl group, or a substituted or unsubstituted aralkyl group, $X^2$ represents a hydrogen atom, and the symbol "n" represents 0, or physiologically acceptable salts thereof; and further preferred examples include (3) those wherein $R^1$ represents a n-propyl group, a n-butyl group, a cyclobutyl group, a cyclopentyl group, a cyclohexyl group, a cyclopropylmethyl group, a cyclopentylmethyl group, an isopropyl group, or a tert-butyl group, $R^2$ represents a n-propyl group or an ethyl group, $R^3$ represents a hydrogen atom, $X^1$ represents a lower alkyl group or a substituted or unsubstituted aralkyl group, $X^2$ represents a hydrogen atom, and the symbol "n" represents 0, or physiologically acceptable salts thereof.

More specifically, the followings can be exemplified as preferred compounds or physiologically acceptable salts thereof suitable as the active ingredient of the medicament of the present invention. Among them, Compound 16, Compounds 18–20, Compound 23, Compound 31, Compound 35, Compound 37, Compound 43, and Compound 55 are particularly preferred. The compounds in free forms or other physiologically acceptable salts of these salts are also preferred. References disclosing each corresponding compound are indicated in the parentheses after the names of compounds. As for Compound 6, a racemate thereof is disclosed in Japanese Patent Unexamined Publication No.3-204880/1991. It should be understood that the active ingredients of the medicaments of the present invention are not limited to the compounds or physiologically acceptable salts thereof listed below. The compounds specifically disclosed in Japanese Patent Unexamined Publication No. 3-204880/1991 or International Publication WO98/15555 or physiologically acceptable salts thereof, as well as those listed below, are preferred as the active ingredient of the medicament of the present invention.

Compound 1: (R)-8-ethyl-7,8-dihydro-2-(3-noradamantyl)-4-propyl-1H-imidazo[2,1-i]purin-5(4H)-one L-tartrate (Journal of Medicinal Chemistry, vol.36, p.2508, 1993)

Compound 2: (S)-8-ethyl-7,8-dihydro-2-(3-noradamantyl)-4-propyl-1H-imidazo[2,1-i]purin-5(4H)-one D-tartrate (Journal of Medicinal Chemistry, vol. 36, p.2508, 1993)

Compound 3: (R)-7,8-dihydro-8-isopropyl-2-(3-noradamantyl)-4-propyl-1H-imidazo[2,1-i]purin-5(4H)-one hydrochloride Compound 4: (S)-7,8-dihydro-8-isopropyl-2-(3-noradamantyl)-4-propyl-1H-imidazo[2,1-i]purin-5(4H)-one hydrochloride Compound 5: 7,8-dihydro-2-(3-noradamantyl)-4-propyl-1H-imidazo[2,1-i]purin-5(4H)-one hydrochloride Compound 6: (R)-2-cyclopentyl-7,8-dihydro-8-methyl-4-propyl-1H-imidazo[2,1-i]purin-5(4H)-one hydrochloride Compound 7: (R)-2-cyclopentyl-8-ethyl-7,8-dihydro-4-propyl-1H-imidazo[2,1-i]purin-5(4H)-one L-tartrate (Japanese Patent Unexamined Publication No. 3-204880/1991)

Compound 8: (S)-2-cyclopentyl-8-ethyl-7,8-dihydro-4-propyl-1H-imidazo[2,1-i]purin-5(4H)-one D-tartrate (Japanese Patent Unexamined Publication No. 3-204880/1991)

Compound 9: (R)-2-cyclopentyl-7,8-dihydro-8-isopropyl-4-propyl-1H-imidazo[2,1-i]purin-5(4H)-one hydrochloride (Japanese Patent Unexamined Publication 3-204880/1991)

Compound 10: (S)-2-cyclopentyl-7,8-dihydro-8-isopropyl-4-propyl-1H-imidazo[2,1-i]purin-5(4H)-one hydrochloride (Japanese Patent Unexamined Publication No. 3-204880/1991)

Compound 11: (R)-2-cyclopentyl-7,8-dihydro-8-isobutyl-4-propyl-1H-imidazo[2,1-i]purin-5(4H)-one L-tartrate Compound 12: (S)-8-tert-butyl-2-cyclopentyl-7,8-dihydro-4-propyl-1H-imidazo[2,1-i]purin-5(4H)-one hydrochloride Compound 13: 8-butyl-2-cyclopentyl-7,8-dihydro-4-propyl-1H-imidazo[2,1-i]purin-5(4H)-one hydrochloride Compound 14: (S)-8-cyclohexylmethyl-2-cyclopentyl-7,8-dihydro-4-propyl-1H-imidazo[2,1-i]purin-5(4H)-one hydrochloride Compound 15: (R)-2-cyclopentyl-7,8-dihydro-8-phenyl-4-propyl-1H-imidazo[2,1-i]purin-5(4H)-one hydrochloride (Japanese Patent Unexamined Publication No. 3-204880/1991)

Compound 16: (R)-8-benzyl-2-cyclopentyl-7,8-dihydro-4-propyl-1H-imidazo[2,1-i]purin-5(4H)-one hydrochloride (Japanese Patent Unexamined Publication No. 3-204880/1991)

Compound 17: (S)-8-benzyl-2-cyclopentyl-7,8-dihydro-4-propyl-1H-imidazo[2,1-i]purin-5(4H)-one hydrochloride (Japanese Patent Unexamined Publication No. 3-204880/1991)

Compound 18: 2-cyclopentyl-8-(4-fluorobenzyl)-7,8-dihydro-4-propyl-1H-imidazo[2,1-i]purin-5(4H)-one hydrochloride Compound 19: 2-cyclopentyl-8-(3-fluorobenzyl)-7,8-dihydro-4-propyl-1H-imidazo[2,1-i]purin-5(4H)-one hydrochloride Compound 20: 8-(4-chlorobenzyl)-2-cyclopentyl-7,8-dihydro-4-propyl-1H-imidazo[2,1-i]purin-5(4H)-one hydrochloride Compound 21: 8-(3-chlorobenzyl)-2-cyclopentyl-7,8-dihydro-4-propyl-1H-imidazo[2,1-i]purin-5(4H)-one hydrochloride Compound 22: 2-cyclopentyl-8-(2,6-dichlorobenzyl)-7,8-dihydro-4-propyl-1H-imidazo[2,1-i]purin-5(4H)-one hydrochloride Compound 23: 8-(4-bromobenzyl)-2-cyclopentyl-7,8-dihydro-4-propyl-1H-imidazo[2,1-i]purin-5(4H)-one hydrochloride Compound 24: 8-(3-bromobenzyl)-2-cyclopentyl-7,8-dihydro-4-propyl-1H-imidazo[2,1-i]purin-5(4H)-one hydrochloride Compound 25: 2-cyclopentyl-7,8-dihydro-8-(4-methoxybenzyl)-4-propyl-1H-imidazo[2,1-i]purin-5(4H)-one hydrochloride Compound 26: 2-cyclopentyl-7,8-dihydro-8-(4-nitrobenzyl)-4-propyl-1H-imidazo[2,1-i]purin-5(4H)-one hydrochloride Compound 27: (R)-8-(4-benzyloxybenzyl)-2-cyclopentyl-7,8-dihydro-4-propyl-1H-imidazo[2,1-i]purin-5(4H)-one hydrochloride Compound 28: (S)-8-(4-benzyloxybenzyl)-2-cyclopentyl-7,8-dihydro-4-propyl-1H-imidazo[2,1-i]purin-5(4H)-one hydrochloride Compound 29: (R)-8-benzyl-2-cyclopentyl-7,8-dihydro-1-methyl-4-propyl-1H-imidazo[2,1-i]purin-5(4H)-one hydrochloride Compound 30: 2-cyclopentyl-7,8-dihydro-8-diphenylmethyl-4-propyl-1H-imidazo[2,1-i]purin-5(4H)-one hydrochloride Compound 31: 2-cyclopentyl-7,8-dihydro-8-phenethyl-4-propyl-1H-imidazo[2,1-i]purin-5(4H)-one hydrochloride Compound 32: (R)-4,8-dibenzyl-2-cyclopentyl-7,8-dihydro-1H-imidazo[2,1-i]purin-5(4H)-one hydrochloride Compound 33: (R)-8-benzyl-7,8-dihydro-4-propyl-1H-imidazo[2,1-i]purin-5(4H)-one hydrochloride Compound 34: (R)-1,8-dibenzyl-7,8-dihydro-4-propyl-1H-imidazo[2,1-i]purin-5(4H)-one hydrochloride Compound 35: (R)-8-benzyl-7,8-dihydro-2,4-dipropyl-1H-imidazo[2,1-i]purin-5(4H)-one hydrochloride Compound 36: (R)-8-benzyl-2-cyclopropyl-7,8-dihydro-4-propyl-1H-imidazo[2,1-i]purin-5(4H)-one hydrochloride Compound 37: (R)-8-benzyl-2-cyclobutyl-7,8-dihydro-4-propyl-1H-imidazo[2,1-i]purin-5(4H)-one hydrochloride Compound 38: (R)-8-benzyl-2-cyclohexyl-7,8-dihydro-4-propyl-1H-imidazo[2,1-i]purin-5(4H)-one hydrochloride Compound 39: (R)-8-benzyl-7,8-dihydro-2-(3-noradamantyl)-4-propyl-1-H-imidazo[2,1-i]purin-5(4H)-one hydrochloride Compound 40: (R)-8-benzyl-2-cyclopentylmethyl-7,8-dihydro-4-propyl-1H-imidazo[2,1-i]purin-5(4H)-one hydrochloride Compound 41: (R)-8-benzyl-7,8-dihydro-2-isopropyl-4-propyl-1H-imidazo[2,1-i]purin-5(4H)-one hydrochloride Compound 42: (R)-8-benzyl-2-(3-furyl)-7,8-dihydro-4-propyl-1H-imidazo[2,1-i]purin-5(4H)-one hydrochloride Compound 43: (R)-8-benzyl-2-tert-butyl-7,8-dihydro-4-propyl-1H-imidazo[2,1-i]purin-5(4H)-one hydrochloride Compound 44: (R)-8-benzyl-7,8-dihydro-4-propyl-2-(3-thienyl)-1H-imidazo[2,1-i]purin-5(4H)-one hydrochloride Compound 45: 8-(4-bromobenzyl)-2-cyclohexyl-7,8-dihydro-4-propyl-1H-imidazo[2,1-i]purin-5(4H)-one hydrochloride Compound 46: 8-(4-chlorobenzyl)-7,8-dihydro-2,4-dipropyl-1H-imidazo[2,1-i]purin-5(4H)-one hydrochloride Compound 47: 8-(4-chlorobenzyl)-2-cyclohexyl-7,8-dihydro-4-propyl-1H-imidazo[2,1-i]purin-5(4H)-one hydrochloride Compound 48: 8-(4-chlorobenzyl)-2-cyclobutyl-7,8-dihydro-4-propyl-1H-imidazo[2,1-i]purin-5(4H)-one hydrochloride Compound 49: 8-(4-fluorobenzyl)-7,8-dihydro-2,4-dipropyl-1H-imidazo[2,1-i]purin-5(4H)-one hydrochloride Compound 50: 2-cyclohexyl-8-(4-fluorobenzyl)-7,8-dihydro-4-propyl-1H-imidazo[2,1-i]purin-5(4H)-one hydrochloride Compound 51: (R)-2-cyclobutyl-8-(4-fluorobenzyl)-7,8-dihydro-4-propyl-1H-imidazo[2,1-i]purin-5(4H)-one hydrochloride Compound 52: 2-butyl-8-(4-fluorobenzyl)-7,8-dihydro-4-propyl-1H-imidazo[2,1-i]purin-5(4H)-one hydrochloride Compound 53: 8-(4-fluorobenzyl)-2-(2-furyl)-7,8-dihydro-4-propyl-1H-imidazo[2,1-i]purin-5(4H)-one hydrochloride Compound 54: (R)-8-(4-fluorobenzyl)-2-(3-furyl)-7,8-dihydro-4-propyl-1H-imidazo[2,1-i]purin-5(4H)-one Compound 55: (R)-2-tert-butyl-8-(4-fluorobenzyl)-7,8-dihydro-4-propyl-1H-imidazo[2,1-i]purin-5(4H)-one hydrochloride Compound 56: 8-(3-fluorobenzyl)-7,8-dihydro-2,4-dipropyl-1H-imidazo[2,1-i]purin-5(4H)-one hydrochloride Compound 57: 2-cyclobutyl-8-(3-fluorobenzyl)-7,8-dihydro-4-propyl-1H-imidazo[2,1-i]purin-5(4H)-one hydrochloride Compound 58: 8-(3-fluorobenzyl)-7,8-dihydro-2-isobutyl-4-propyl-1H-imidazo[2,1-i]purin-5(4H)-one Compound 59: 2-(4-bromophenyl)-8-(3-fluorobenzyl)-7,8-dihydro-4-propyl-1H-imidazo[2,1-i]purin-5(4H)-one hydrochloride Compound 60: 8-(2-fluorobenzyl)-7,8-dihydro-2-isobutyl-4-propyl-1H-imidazo[2,1-i]purin-5(4H)-one Compound 61: 2-cyclopentyl-7,8-dihydro-8-(3-methylbenzyl)-4-propyl-1H-imidazo[2,1-i]purin-5(4H)-one Compound 62: 2-cyclopentyl-7,8-dihydro-8-(3-iodobenzyl)-4-propyl-1H-imidazo[2,1-i]purin-5(4H)-one hydrochloride Compound 63: 2-cyclopentyl-8-(2,3-difluorobenzyl)-7,8-dihydro-4-propyl-1H-imidazo[2,1-i]purin-5(4H)-one hydrochloride Compound 64: 2-cyclopentyl-8-(2,5-difluorobenzyl)-7,8-dihydro-4-propyl-1H-imidazo[2,1-i]purin-5(4H)-one hydrochloride Compound 65: 2-cyclopentyl-8-(2,5-dichlorobenzyl)-7,8-dihydro-4-propyl-1H-imidazo[2,1-i]purin-5(4H)-one hydrochloride Compound 66: (S)-8-tert-butyl-7,8-dihydro-2-(3-noradamantyl)-4-propyl-1H-imidazo[2,1-i]purin-5(4H)-one hydrochloride Compound 67: (S)-8-tert-butyl-2-(3-furyl)-7,8-dihydro-4-propyl-1H-imidazo[2,1-i]purin-5(4H)-one Compound 68: (S)-8-tert-butyl-2-(3,5-dimethylisoxazol-4-yl)-7,8-dihydro-4-propyl-1H-imidazo[2,1-i]purin-5(4H)-one hydrochloride Compound 69: (S)-7,8-dihydro-2,8-diisopropyl-4-propyl-1H-imidazo[2,1-i]purin-5(4H)-one hydrochloride Compound 70: 8-(3-cyanobenzyl)-2-cyclopentyl-7,8-dihydro-4-propyl-1H-imidazo[2,1-i]purin-5(4H)-one Compound 71: (R)-8-benzyl-2-cyclopentyl-4-ethyl-7,8-dihydro-1H-imidazo[2,1-i]purin-5(4H)-one hydrochloride Compound 72: (R)-8-benzyl-2-cyclopentyl-4-cyclopropylmethyl-7,8-dihydro-1H-imidazo[2,1-i]purin-5(4H)-one Compound 73: (R)-8-benzyl-2-cyclopropylmethyl-7,8-dihydro-4-propyl-1H-imidazo-[2,1-i]purin-5(4H)-one hydrochloride Compound 74: 8-(3-carboxybenzyl)-2-cyclopentyl-7,8-dihydro-4-propyl-1H-imidazo[2,1-i]purin-5(4H)-one Compound 75: 2-cyclopentyl-8-(α, α-dimethylbenzyl)-7,8-dihydro-4-propyl-1H-imidazo[2,1-i]purin-5(4H)-one Compound 76: (R)-2-cyclopentyl-7,8-dihydro-8-(4-hydroxybenzyl)-4-propyl-1H-imidazo[2,1-i]purin-5(4H)-one Compound 77: (R)-8-benzyl-7,8-dihydro-4-propyl-2-(3-pyridyl)-1H-imidazo[2,1-i]purin-5(4H)-one Compound 78: (R)-8-benzyl-7,8-dihydro-2-phenyl-4-propyl-1H-imidazo[2,1-i]purin-5(4H)-one Compound 79: (R)-8-benzyl-7,8-dihydro-4-propyl-2-(2,2,3,3-tetramethylcyclopropyl)-1H-imidazo[2,1-i]purin-5(4H)-one Compound 80: (R)-8-benzyl-7,8-dihydro-2-(3,4-methylenedioxyphenyl)-4-propyl-1H-imidazo[2,1-i]purin-5(4H)-one Compound 81: (R)-8-benzyl-7,8-dihydro-4-propyl-2-(4-pyridyl)-1H-imidazo[2,1-i]purin-5(4H)-one Compound 82: (R)-8-benzyl-7,8-dihydro-4-propyl-2-(2-pyrazyl)-1H-imidazo[2,1-i]purin-5(4H)-one Compound 83: (R)-8-benzyl-7,8-dihydro-4-propyl-2-(2-thienyl)-1H-imidazo[2,1-i]purin-5(4H)-one Compound 84: (R)-8-benzyl-2-cyclopentyl-7,8-dihydro-4-methyl-1H-imidazo[2,1-i]purin-5(4H)-one Compound 85: (R)-8-benzyl-2-cyclopentyl-7,8-dihydro-4-phenyl-1H-imidazo[2,1-i]purin-5(4H)-one Compound 86: 8-(4-tert-butylbenzyl)-2-cyclopentyl-7,8-dihydro-4-propyl-1H-imidazo[2,1-i]purin-5(4H)-one Compound 87: 2-cyclopentyl-7,8-dihydro-8-(2-phenylbenzyl)-4-propyl-1H-imidazo[2,1-i]purin-5(4H)-one Compound 88: 2-cyclopentyl-7,8-dihydro-4-propyl-8-(3-trifluoromethylbenzyl)-1H-imidazo[2,1-i]purin-5(4H)-one Compound 89: 2-cyclopentyl-8-[3-(2-fluorophenoxy)benzyl]-7,8-dihydro-4-propyl-1H-imidazo[2,1-i]purin-5(4H)-one Compound 90: 2-cyclopentyl-7,8-dihydro-8-(3-phenoxybenzyl)-4-propyl-1H-imidazo[2,1-i]purin-5(4H)-one Compound 91: 2-cyclopentyl-7,8-dihydro-4-propyl-8-(3-trifluoromethoxybenzyl)-1H-imidazo[2,1-i]purin-5(4H)-one Compound 92: 8-[3,5-bis(trifluoromethyl)benzyl]-2-cyclopentyl-7,8-dihydro-4-propyl-1H-imidazo[2,1-i]purin-5(4H)-one Compound 93: 8-benzyl-2-cyclopentyl-7,8-dihydro-8-methyl-4-propyl-1H-imidazo[2,1-i]purin-5(4H)-one

TABLE 1

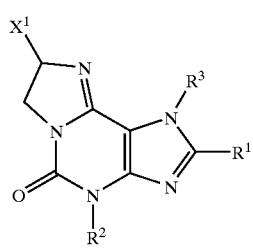

| Compound No. | $R^1$ | $R^2$ | $R^3$ | $X^1$ | $X^2$ |
|---|---|---|---|---|---|
| 1 | adamantyl | $(CH_2)_2CH_3$ | H | $H_3C-$ | |
| 2 | adamantyl | $(CH_2)_2CH_3$ | H | $H_3C-$ (wedge) | |
| 3 | adamantyl | $(CH_2)_2CH_3$ | H | $(CH_3)_2CH-$ | |

TABLE 1-continued
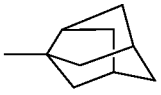
| Compound No. | R¹ | R² | R³ | X¹ | X² |
|---|---|---|---|---|---|
| 4 |  | (CH₂)₂CH₃ | H | 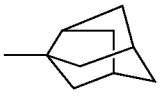 | |
| 5 | 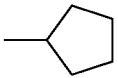 | (CH₂)₂CH₃ | H | H | |
| 6 |  | (CH₂)₂CH₃ | H | 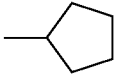 | |
| 7 |  | (CH₂)₂CH₃ | H |  | |
| 8 | 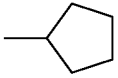 | (CH₂)₂CH₃ | H |  | |
| 9 | 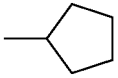 | (CH₂)₂CH₃ | H |  | |
| 10 |  | (CH₂)₂CH₃ | H | 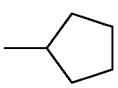 | |
| 11 |  | (CH₂)₂CH₃ | H | 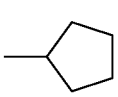 | |
| 12 | 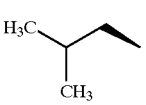 | (CH₂)₂CH₃ | H | 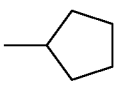 | |
| 13 | 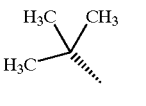 | (CH₂)₂CH₃ | H | 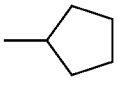 | |
| 14 | 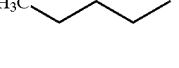 | (CH₂)₂CH₃ | H | 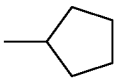 | |
| 15 | 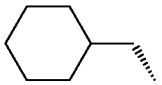 | (CH₂)₂CH₃ | H | 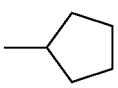 | |

TABLE 1-continued
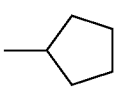
| Compound No. | R¹ | R² | R³ | X¹ | X² |
|---|---|---|---|---|---|
| 16 | 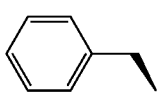 | (CH₂)₂CH₃ | H | 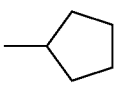 | |
| 17 | 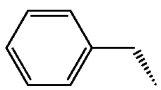 | (CH₂)₂CH₃ | H | 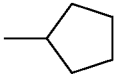 | |
| 18 | 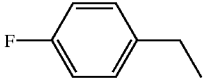 | (CH₂)₂CH₃ | H | 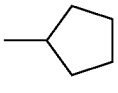 | |
| 19 | 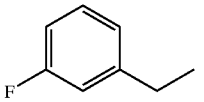 | (CH₂)₂CH₃ | H | 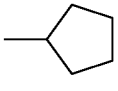 | |
| 20 | 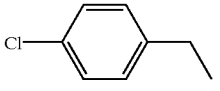 | (CH₂)₂CH₃ | H | 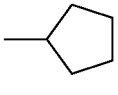 | |
| 21 | 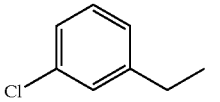 | (CH₂)₂CH₃ | H | 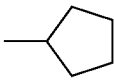 | |
| 22 | 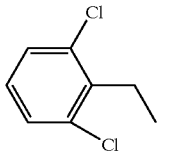 | (CH₂)₂CH₃ | H | 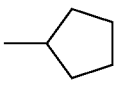 | |
| 23 | 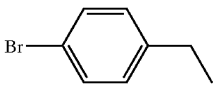 | (CH₂)₂CH₃ | H | 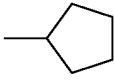 | |
| 24 | 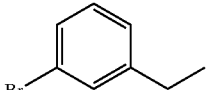 | (CH₂)₂CH₃ | H | 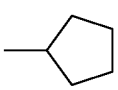 | |
| 25 | 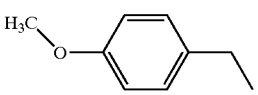 | (CH₂)₂CH₃ | H | 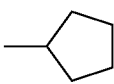 | |
| 26 | 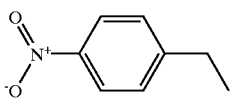 | (CH₂)₂CH₃ | H | | |

TABLE 1-continued

[Structure: tricyclic imidazo-purinone core with substituents X¹, R³, R¹, R², and X² positions]

| Compound No. | R¹ | R² | R³ | X¹ | X² |
|---|---|---|---|---|---|
| 27 | cyclopentyl | (CH₂)₂CH₃ | H | benzyl | 4-(benzyloxy)phenylethyl |
| 28 | cyclopentyl | (CH₂)₂CH₃ | H | benzyl | 4-(benzyloxy)phenylethyl (stereo) |
| 29 | cyclopentyl | (CH₂)₂CH₃ | CH₃ | benzyl | phenylethyl |
| 30 | cyclopentyl | (CH₂)₂CH₃ | H | benzyl | 2,2-diphenylethyl |
| 31 | cyclopentyl | (CH₂)₂CH₃ | H | benzyl | 3-phenylpropyl |
| 32 | cyclopentyl | phenylethyl | | benzyl | phenylethyl |
| 33 | H | (CH₂)₂CH₃ | H | benzyl | phenylethyl |
| 34 | H | (CH₂)₂CH₃ | | benzyl | phenylethyl |
| 35 | CH₂CH₂CH₃ | (CH₂)₂CH₃ | H | benzyl | phenylethyl |
| 36 | cyclopropyl | (CH₂)₂CH₃ | H | benzyl | phenylethyl |

TABLE 1-continued
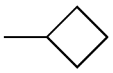
| Compound No. | R¹ | R² | R³ | X¹ | X² |
|---|---|---|---|---|---|
| 37 | 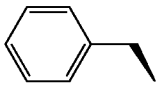 | (CH$_2$)$_2$CH$_3$ | H | | 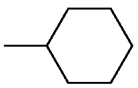 |
| 38 | 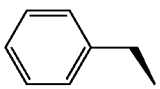 | (CH$_2$)$_2$CH$_3$ | H | | 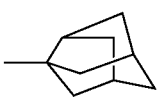 |
| 39 | 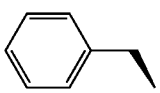 | (CH$_2$)$_2$CH$_3$ | H | | 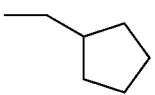 |
| 40 | 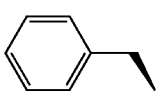 | (CH$_2$)$_2$CH$_3$ | H | | 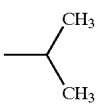 |
| 41 | 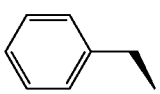 | (CH$_2$)$_2$CH$_3$ | H | | 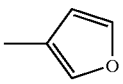 |
| 42 | 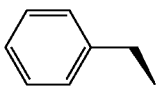 | (CH$_2$)$_2$CH$_3$ | H | | 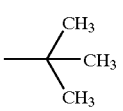 |
| 43 | 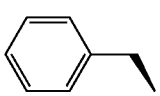 | (CH$_2$)$_2$CH$_3$ | H | | 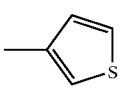 |
| 44 | 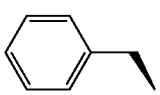 | (CH$_2$)$_2$CH$_3$ | H | | 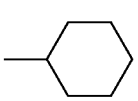 |
| 45 | 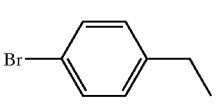 | (CH$_2$)$_2$CH$_3$ | H | | 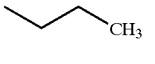 |
| 46 | 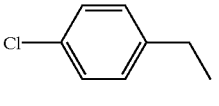 | (CH$_2$)$_2$CH$_3$ | H | | 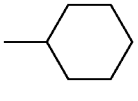 |
| 47 | 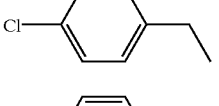 | (CH$_2$)$_2$CH$_3$ | H | | 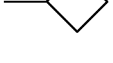 |
| 48 | 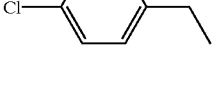 | (CH$_2$)$_2$CH$_3$ | H | | |

TABLE 1-continued

[Structure: tricyclic imidazo-purine core with substituents X¹, R³, R¹, R², O, and implied X² position]

| Compound No. | R¹ | R² | R³ | X¹ | X² |
|---|---|---|---|---|---|
| 49 | -CH₂CH₂CH₂CH₃ (n-butyl) | (CH₂)₂CH₃ | H | | 4-fluorophenylethyl |
| 50 | cyclohexylmethyl | (CH₂)₂CH₃ | H | | 4-fluorophenylethyl |
| 51 | cyclobutylmethyl | (CH₂)₂CH₃ | H | | 4-fluorophenylethyl |
| 52 | -(CH₂)₄CH₃ (n-pentyl) | (CH₂)₂CH₃ | H | | 4-fluorophenylethyl |
| 53 | furan-2-ylmethyl | (CH₂)₂CH₃ | H | | 4-fluorophenylethyl |
| 54 | furan-3-ylmethyl | (CH₂)₂CH₃ | H | | 4-fluorophenylethyl |
| 55 | neopentyl (-CH₂C(CH₃)₃) | (CH₂)₂CH₃ | H | | 4-fluorophenylethyl |
| 56 | -CH₂CH₂CH₂CH₃ (n-butyl) | (CH₂)₂CH₃ | H | | 3-fluorophenylethyl |
| 57 | cyclobutylmethyl | (CH₂)₂CH₃ | H | | 3-fluorophenylethyl |
| 58 | isobutyl (-CH₂CH(CH₃)₂) | (CH₂)₂CH₃ | H | | 3-fluorophenylethyl |
| 59 | 4-bromobenzyl | (CH₂)₂CH₃ | H | | 3-fluorophenylethyl |

TABLE 1-continued
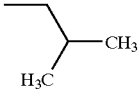
| Compound No. | R¹ | R² | R³ | X¹ | X² |
|---|---|---|---|---|---|
| 60 | 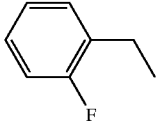 | (CH$_2$)$_2$CH$_3$ | H | 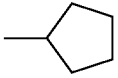 | |
| 61 | 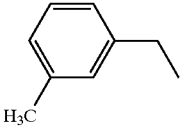 | (CH$_2$)$_2$CH$_3$ | H | 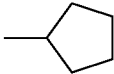 | |
| 62 | 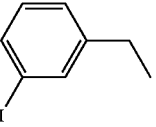 | (CH$_2$)$_2$CH$_3$ | H | 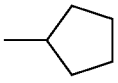 | |
| 63 | 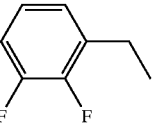 | (CH$_2$)$_2$CH$_3$ | H | 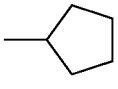 | |
| 64 | 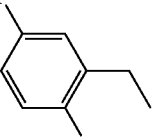 | (CH$_2$)$_2$CH$_3$ | H | 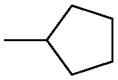 | |
| 65 | 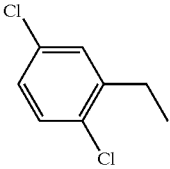 | (CH$_2$)$_2$CH$_3$ | H | 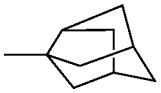 | |
| 66 | 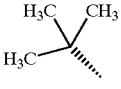 | (CH$_2$)$_2$CH$_3$ | H | 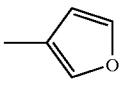 | |
| 67 | 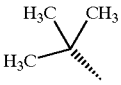 | (CH$_2$)$_2$CH$_3$ | H | | |

TABLE 1-continued
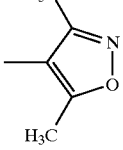
| Compound No. | R¹ | R² | R³ | X¹ | X² |
|---|---|---|---|---|---|
| 68 | 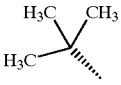 | (CH$_2$)$_2$CH$_3$ | H | 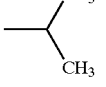 | |
| 69 |  | (CH$_2$)$_2$CH$_3$ | H | 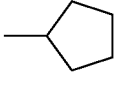 | |
| 70 | 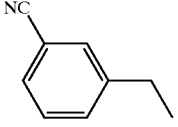 | (CH$_2$)$_2$CH$_3$ | H | 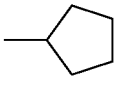 | |
| 71 | 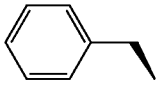 | CH$_2$CH$_3$ | H | 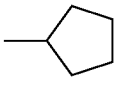 | |
| 72 |  | 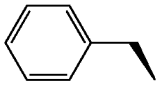 | H |  | |
| 73 | 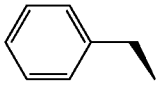 | (CH$_2$)$_2$CH$_3$ | H | 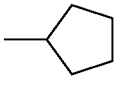 | |
| 74 | 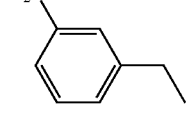 | (CH$_2$)$_2$CH$_3$ | H | 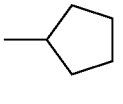 | |
| 75 | 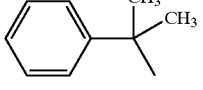 | (CH$_2$)$_2$CH$_3$ | H | 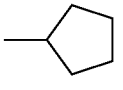 | |
| 76 | 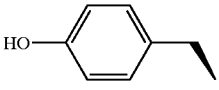 | (CH$_2$)$_2$CH$_3$ | H | 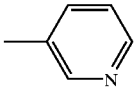 | |
| 77 | 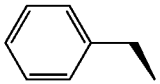 | (CH$_2$)$_2$CH$_3$ | H | 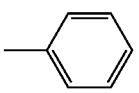 | |
| 78 | 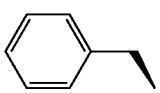 | (CH$_2$)$_2$CH$_3$ | H | 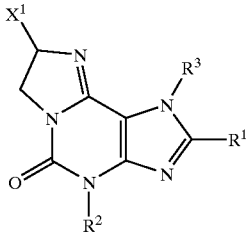 | |

TABLE 1-continued

[Structure: bicyclic imidazo-purine core with substituents X¹, R³, R¹, R², O, and X² positions]

| Compound No. | R¹ | R² | R³ | X¹ | X² |
|---|---|---|---|---|---|
| 79 | 2,2,3,3-tetramethylcyclopropyl | (CH₂)₂CH₃ | H | benzyl | |
| 80 | 3,4-methylenedioxyphenylmethyl | (CH₂)₂CH₃ | H | benzyl | |
| 81 | 4-pyridylmethyl | (CH₂)₂CH₃ | H | benzyl | |
| 82 | pyrazin-2-ylmethyl | (CH₂)₂CH₃ | H | benzyl | |
| 83 | 2-thienylmethyl | (CH₂)₂CH₃ | H | benzyl | |
| 84 | cyclopentylmethyl | CH₃ | H | benzyl | |
| 85 | cyclopentylmethyl | C₆H₅ | H | benzyl | |
| 86 | cyclopentylmethyl | (CH₂)₂CH₃ | H | 4-tert-butylbenzyl | H |
| 87 | cyclopentylmethyl | (CH₂)₂CH₃ | H | 2-phenylbenzyl | H |
| 88 | cyclopentylmethyl | (CH₂)₂CH₃ | H | 3-(trifluoromethyl)benzyl | H |

TABLE 1-continued

| Compound No. | R¹ | R² | R³ | X¹ | X² |
|---|---|---|---|---|---|
| 89 | cyclopentyl | $(CH_2)_2CH_3$ | H | 2-fluorophenoxy-3-ethylphenyl | H |
| 90 | cyclopentyl | $(CH_2)_2CH_3$ | H | phenoxy-3-ethylphenyl | H |
| 91 | cyclopentyl | $(CH_2)_2CH_3$ | H | 3-(F₃CO)-phenylethyl | H |
| 92 | cyclopentyl | $(CH_2)_2CH_3$ | H | 3,5-bis(F₃C)-phenylethyl | H |
| 93 | cyclopentyl | $(CH_2)_2CH_3$ | H | $CH_3$ | benzyl |

The compounds represented by the general formula (I) or physiologically acceptable salts thereof have insulin secretion enhancing action in cultured β-cells and hypoglycemic action in rats, and accordingly, they are useful as an active ingredient of the medicament for the treatment of diabetes. Further, they are useful as an active ingredient of the medicament for the prophylactic and/or therapeutic treatment of various complications of diabetes, for example, retinopathy, nephropathy, neurosis and the like. As the active ingredient of the medicament of the present invention, one or more substances selected from the group consisting of the compounds represented by the general formula (I) and physiologically acceptable salts thereof, and hydrates thereof and solvates thereof can be used. Although the aforementioned substances, per se, may be administered, it is generally desirable to provide the medicament in a form of a pharmaceutical composition comprising the aforementioned substance as the active ingredient and one or more pharmaceutical additives. The medicament of the present invention can be administered to human and other mammals.

The form of the pharmaceutical composition is not particularly limited, and an appropriate form most suitable for a purpose of the prophylactic or therapeutic treatment can be selected from forms of pharmaceutical preparations for oral or parenteral administration. Examples of pharmaceutical preparations suitable for oral administration include tablets, capsules, powders, granules, subtilized granules, syrups, solutions, emulsions, suspensions, chewable formulations and the like. Examples of pharmaceutical preparations suitable for parenteral administration include injections (for subcutaneous injection, intramuscular injection, intravenous injection or the like), drip infusions, inhalants, sprays, suppositories, transdermal or transmucosal preparations in the forms of gel, ointment or the like, transdermal preparations in the forms of patch, tape or the like. However, the preparations are not limited to these examples.

Liquid preparations suitable for oral administration such as solutions, emulsions and syrups can be prepared by using water, saccharides such as sucrose, sorbitol and fructose, glycols such as polyethylene glycol and propylene glycol, oils such as sesame oil, olive oil and soybean oil, preservatives such as p-hydroxybenzoic acid esters, flavors such as strawberry flavor and peppermint or the like. For the preparation of solid preparations such as capsules, tablets, powders and granules, excipients such as lactose, glucose, sucrose and mannitol, disintegrating agents such as starch and sodium alginate, lubricants such as magnesium stearate and talc, binders such as polyvinyl alcohol, hydroxypropylcellulose and gelatin, surface active agents such as fatty acid esters, plasticizers such as glycerin or the like may be used.

Pharmaceutical preparations for injection or drip infusion, which are suitable for parenteral administration, contain the aforementioned substance as the active ingredient preferably in a sterilized aqueous medium isotonic with blood of a recipient in a dissolved or suspended state. For example, as for injections, a solution can be prepared by using an aqueous medium consisting of saline, a glucose solution, or a mixture of saline and a glucose solution. Preparations for enteral administration can be prepared, for example, by using a carrier such as cacao butter or hard fat, and are provided as suppositories. Further, for the preparation of sprays, a carrier may be used which can disperse the aforementioned substance as the active ingredient as fine particles, and facilitate adsorption of the active ingredient without stimulating mucosae of oral cavity and respiratory tract of recipients. Specifically, examples of the carrier include lactose and glycerol. Depending on the properties of the substance as the active ingredient and the carrier, pharmaceutical preparations in forms of aerosol, dry powder and the like can be prepared. To these pharmaceutical preparations for parenteral administration, one or more auxiliary ingredients selected from glycols, oils, flavors, preservatives, excipients, disintegrating agents, lubricants, binders, surface active agents, plasticizers and the like may also be added.

Dose and frequency of administration of the medicament of the present invention may preferably be increased or decreased depending on various factors such as type and severity of diseases, dosage form, conditions of patients such as age and body weight, and presence or absence of complications. In general, the medicament may preferably be administered in an amount of 1 to 1000 mg/kg per day for an adult dividedly as three or four times of administrations.

According to another aspect of the present invention, there are provided the compounds of the general formula (I):

(1) wherein $R^1$ represents a 3-noradamantyl group, $R^2$ represents a n-propyl group, $R^3$ represents a hydrogen atom, $X^1$ represents a hydrogen atom, a tert-butyl group, an isopropyl group, or a benzyl group, $X^2$ represents a hydrogen atom, and the symbol "n" represents 0;

(2) wherein $R^1$ represents a cyclopentyl group, $R^2$ represents a n-propyl group, $R^3$ represents a hydrogen atom, $X^1$ represents a n-butyl group, an isobutyl group, a tert-butyl group, a cyclohexylmethyl group, an aralkyl group whose alkyl moiety is substituted or an unsubstituted aralkyl group (except for a benzyl group), or an aralkyl group (preferably a benzyl group) having one or more substituents (preferably one or two, more preferably one) selected from the group consisting of a halogen atom, a substituted or unsubstituted lower alkyl group, a lower alkoxyl group (preferably a methoxy group), an aralkyloxy group (preferably a benzyloxy group), a carboxyl group, a cyano group, a hydroxyl group, and a nitro group on the ring, $X^2$ represents a hydrogen atom, and the symbol "n" represents 0;

(3) wherein $R^1$ represents a cyclopentyl group, $R^2$ represents a n-propyl group, $R^3$ represents a lower alkyl group (preferably a methyl group), $X^1$ represents a substituted or unsubstituted aralkyl group (preferably a benzyl group), $X^2$ represents a hydrogen atom, and the symbol "n" represents 0;

(4) wherein $R^1$ represents a cyclopentyl group, $R^2$ represents a substituted or unsubstituted aralkyl group (preferably a benzyl group), a lower alkyl group (except for a n-propyl group; preferably a cyclopropylmethyl group or a linear lower alkyl group) or a substituted or unsubstituted aryl group (preferably a phenyl group), $R^3$ represents a hydrogen atom, $X^1$ represents a substituted or unsubstituted aralkyl group (preferably a benzyl group), $X^2$ represents a hydrogen atom, and the symbol "n" represents 0;

(5) wherein $R^1$ represents a hydrogen atom, $R^2$ represents a n-propyl group, $R^3$ represents a hydrogen atom, or a substituted or unsubstituted aralkyl group (preferably a benzyl group), $X^1$ represents a substituted or unsubstituted aralkyl group (preferably a benzyl group), $X^2$ represents a hydrogen atom, and the symbol "n" represents 0;

(6) wherein $R^1$ represents a lower alkyl group (except for a cyclopentyl group), a substituted or unsubstituted aromatic heterocyclic group, or a substituted or unsubstituted aryl group, $R^2$ represents a n-propyl group, $R^3$ represents a hydrogen atom, $X^1$ represents a substituted or unsubstituted aralkyl group (preferably a benzyl group), $X^2$ represents a hydrogen atom, and the symbol "n" represents 0;

(7) wherein $R^1$ represents a linear or branched lower alkyl group (preferably an isopropyl group) or a substituted or unsubstituted aromatic heterocyclic group, $R^2$ represents a n-propyl group, $R^3$ represents a hydrogen atom, $X^1$ represents a lower alkyl group (except for a methyl group; preferably an isopropyl group, or an isobutyl group, a t-butyl group), $X^2$ represents a hydrogen atom, and the symbol "n" represents 0; and (8) wherein $R^1$ represents a cyclopentyl group, $R^2$ represents a n-propyl group, $R^3$ represents a hydrogen atom, $X^1$ represents a methyl group, $X^2$ represents a substituted or unsubstituted aralkyl group, and the symbol "n" represents 0.

Specific examples of these compounds include, for example, Compounds 3–5, Compounds 11–14, and Compound 18 to Compound 93.

As preferred compounds, there are provided:
the aforementioned compounds wherein $R^1$ represents a cyclopentyl group, $R^2$ represents a n-propyl group, $R^3$ represents a hydrogen atom, $X^1$ represents an aralkyl group (preferably a benzyl group) having one or more (preferably one) halogen atoms on the ring or an unsubstituted aralkyl group (except for a benzyl group), $X^2$ represents a hydrogen atom, and the symbol "n" represents 0;

the aforementioned compounds wherein $R^1$ represents a cyclopentyl group, $R^2$ represents a linear or branched lower alkyl group (except for a n-propyl group), $R^3$ represents a hydrogen atom, $X^1$ represents a substituted or unsubstituted aralkyl group (preferably a benzyl group), $X^2$ represents a hydrogen atom, and the symbol "n" represents 0; and the aforementioned compounds wherein $R^1$ represents a lower alkyl group (except for a cyclopentyl group), $R^2$ represents a n-propyl group, $R^3$ represents a hydrogen atom, $X^1$ represents a substituted or unsubstituted aralkyl group (preferably a benzyl group), $X^2$ represents a hydrogen atom, and the symbol "n" represents 0;

Particularly preferred compounds are:
the aforementioned compounds where $R^1$ represents a cyclopentyl group, $R^2$ represents an ethyl group, $R^3$ represents a hydrogen atom, $X^1$ represents a substituted or unsubstituted aralkyl group (preferably a benzyl group), $X^2$ represents a hydrogen atom, and the symbol "n" represents 0; and the aforementioned compounds wherein $R^1$ represents a tert-butyl group, $R^2$ represents a n-propyl group, $R^3$ represents a hydrogen atom, $X^1$ represents a substituted or unsubstituted aralkyl group (preferably a benzyl group), $X^2$ represents a hydrogen atom, and the symbol "n" represents 0.

As salts of the aforementioned compounds, those explained above can be used. It should be understood that, besides the aforementioned compounds in free forms and physiologically acceptable salts thereof, any hydrates and solvates thereof fall within the scope of the present invention. Further, any isomers, mixtures of isomers, racemates and the like also fall within the scope of the present invention. These compounds and salts thereof are useful as, for example, the active ingredient of the medicament of the present invention. However, utilities of the compounds of the present invention and salts thereof are not limited to said particular utility.

BEST MODE FOR CARRYING OUT THE INVENTION

EXAMPLES

The present invention will be explained more specifically with reference to the following examples. However, the scope of the present invention is not limited to the following examples.

Formulation Example 1

Tablet

Tablets consisting of the following composition were prepared in a conventional manner.

| Formulation | |
|---|---|
| Compound 16 | 20 mg |
| Lactose | 143.4 mg |
| Potato starch | 30 mg |
| Hydroxypropylcellulose | 6 mg |
| Magnesium stearate | 0.6 mg |
| | 200 mg |

Formulation Example 2

Capsule

Capsules consisting of the following composition were prepared in a conventional manner.

| Formulation | |
|---|---|
| Compound 16 | 20 mg |
| Avicell | 99.5 mg |
| Magnesium stearate | 0.5 mg |
| | 120 mg |

Formulation Example 3

Injection

Injections consisting of the following composition were prepared in a conventional manner.

| Formulation | |
|---|---|
| Compound 16 | 2 mg |
| Purified soybean oil | 200 mg |
| Purified yolk lecithin | 24 mg |
| Glycerol for injection | 50 mg |
| Distilled water for injection | 1.72 ml |
| | 2.00 ml |

Formulation Example 4

Suppository for Anus

Preparations for rectal administration consisting of the following composition were prepared in a conventional manner.

| Formulation | |
|---|---|
| Compound 16 | 2.5 mg |
| Witepsol H15 | 678.8 mg |
| Witepsol E75 | 290.9 mg |
| Potassium primary phosphate | 13.6 mg |
| Sodium secondary phosphate | 14.2 mg |
| | 1,000 mg |

Example 1

Compound 3

To 6-methylthio-8-(3-noradamantyl)-3-propyl-7H-purin-2(3H)-one (Compound 3a, 3.06 g, 8.90 mmol) obtained by a known method [Journal of Medicinal Chemistry, vol. 36, p.2508, 1993] was added (R)-valinol (5.7 ml, a 4.66 M solution in dimethyl sulfoxide, 3.0 eq.) under an argon flow, and the mixture was heated at 150° C. for 3.5 hours with stirring. The reaction solution was poured into a 10% aqueous solution of ammonium chloride, and the mixture was extracted with chloroform. The organic layer was washed with a saturated aqueous solution of sodium chloride and dried, and then the solvent was evaporated. The residue was purified by silica gel column chromatography (chloroform:methanol=10:1) to obtain an adduct (2.97 g, 84%). To the adduct (2.78 g, 6.97 mmol) was added thionyl chloride (30 ml), and the mixture was heated at 60° C. for 3 hours with stirring. After the excessive thionyl chloride was evaporated, the reaction mixture was neutralized with sodium hydrogen carbonate and extracted with chloroform. The organic layer was washed with a saturated aqueous solution of sodium chloride and dried, and the solvent was evaporated. The residue was purified by silica gel column chromatography (chloroform:methanol=50:1), and the solvent was evaporated. A methanolic solution of hydrochloric acid was added to the residue and the solvent was evaporated. The residue was crystallized from ethyl acetate/hexane to obtain Compound 3 (2.25 g, 77%).

Yield: 65%

Melting point: 105–107° C. (cyclohexane) Optical rotation: $[\alpha]_D^{20}$ +36.9° {c 1.00, $CH_3OH$, >99% ee [CHIRALCEL OD column (4.6×250 mm), Daicel Chemical Industries, elution solvent: hexane/ethanol/diethylamine= 95/5/0.05]}

$^1$H NMR (270 MHz, CDCl$_3$) δ: 0.98 (t, 3H, J=7.4 Hz), 1.05 (d, 3H, J=6.6 Hz), 1.14 (d, 3H, J=7.0 Hz), 1.65–2.10 (m, 11H), 2.30 (m, 2H), 2.41 (m, 2H), 2.69 (t, 1H, J=6.0 Hz), 4.01 (dd, 1H, J=11.0, 7.0 Hz), 4.09–4.22 (m, 3H), 4.32 (dd, 1H, J=11.0, 10.0 Hz)

IR (KBr): 1714, 1688, 1591 cm$^{-1}$

EI-MS: m/e 381 (M$^+$)

Elemental analysis: for C$_{22}$H$_{31}$N$_5$O.HCl.0.4H$_2$O

Calculated (%): C, 63.87; H, 8.26; N, 15.26 Found (%): C, 63.92; H, 8.19; N, 15.20

Example 2

Compound 4

Compound 4 was obtained from Compound 3a and (S)-valinol in the same manner as Example 1.

Yield: 57%

Melting point: 108–110° C. (cyclohexane)

Optical rotation: [α]$_D^{20}$–30.8° {c 1.00, CH$_3$OH, >99% ee [CHIRALCEL OD column (4.6×250 mm), Daicel Chemical Industries, elution solvent: hexane/ethanol/diethylamine=95/5/0.05]}

Elemental analysis: for C$_{22}$H$_{31}$N$_5$O HCl.0.25C$_6$H$_{12}$

Calculated (%): C, 64.29; H, 8.04; N, 15.95 Found (%): C, 63.72; H, 8.30; N, 15.43

Example 3

Compound 5

Compound 5 was obtained from Compound 3a and 2-aminoethanol in the same manner as Example 1.

Yield: 21%

Melting point: 274–276° C. (ethyl acetate/toluene)

$^1$H NMR (270 MHz, CDCl$_3$) δ: 0.99 (t, 3H, J=7.4 Hz), 1.67–2.08 (m, 12H), 2.20–2.28 (m, 2H), 2.40–2.43 (m, 2H), 2.71 (t, 1H, J=6.0 Hz), 4.09–4.20 (m, 4H), 4.27–4.40 (m, 2H)

IR (KBr): 1719, 1669, 1590 cm$^{-1}$

EI-MS: m/e 339 (M$^+$)

Elemental analysis: for C$_{19}$H$_{25}$N$_5$O.HCl.0.5H$_2$O

Calculated (%): C, 59.29; H, 7.07; N, 18.19 Found (%): C, 59.31; H, 7.24; N, 18.07

Example 4

Compound 6

Compound 6 was obtained from 8-cyclopentyl-6-methylthio-3-propyl-7H-purin-2(3H)-one (Compound 6a, Journal of Heterocyclic Chemistry, vol. 30, p.241, 1993) and (R)-alaninol in the same manner as Example 1.

Yield: 43%

Melting point: 218–219° C. (ethyl acetate/cyclohexane)

Optical rotation: [α]$_D^{20}$ +41.5° {c 1.00, CH$_3$OH, 96% ee [CHIRALCEL OD column (4.6×250 mm), Daicel Chemical Industries, elution solvent: hexane/ethanol/diethylamine=95/5/0.05]}

Elemental analysis: for C$_{16}$H$_{23}$N$_5$O.HCl.0.2H$_2$O

Calculated (%): C, 56.28; H, 7.20; N, 20.51 Found (%): C, 56.14; H, 7.45; N, 20.33

Example 5

Compound 7

Compound 7 was obtained from Compound 6a and (R)-2-amino-1-butanol in the same manner as Example 1 except that the compound was obtained as L-tartrate instead of hydrochloride.

Yield: 18%

Melting point: 209° C. (isopropanol)

Optical rotation: [α]$_D^{20}$+4.2° {c 1.00, dioxane, 95% ee [CHIRALCEL OD column (4.6×250 mm), Daicel Chemical Industries, elution solvent: hexaneIethanol/diethylamine=95/5/0.05]}

Elemental analysis: for C$_{16}$H$_{23}$N$_5$O.C$_4$H$_6$O$_6$

Calculated (%): C, 54.18; H, 6.71; N, 15.04 Found (%): C, 54.47; H, 6.60; N, 14.68

Example 6

Compound 8

Compound 8 was obtained from Compound 6a and (S)-2-amino-1-butanol in the same manner as Example 1 except that the compound was obtained as D-tartrate instead of hydrochloride.

Yield: 9%

Melting point: 210–212° C. (isopropanol)

Optical rotation: [α]$_D^{20}$–5.3° {c 1.00, dioxane, >99% ee [CHIRALCEL OD column (4.6×250 mm), Daicel Chemical Industries, elution solvent: hexane/ethanol/diethylamine=95/5/0.05]}

Elemental analysis: for C$_{16}$H$_{23}$N$_5$O.C$_4$H$_6$O$_6$

Calculated (%): C, 54.18; H, 6.71; N, 15.04 Found (%): C, 53.74; H, 6.60; N, 14.88

Example 7

Compound 9

Compound 9 was obtained from Compound 6a and (R)-valinol in the same manner as Example 1.

Yield: 26%

Melting point: 116–118° C. (toluene/cyclohexane)

Optical rotation: [αa]$_D^{20}$+51.1° {c 1.00, CH$_3$OH, >99% ee [CHIRALCEL OD column (4.6×250 mm), Daicel Chemical Industries, elution solvent: hexane/ethanol/diethylamine=95/5/0.05]}

$^1$H NMR (270 MHz, CDCl$_3$) δ: 0.90–1.15 (m, 9H), 1.60–2.00 (m, 6H), 2.10–2.25 (m, 4H), 3.20–3.40 (m, 1H), 4.00–4.40 (m, 6H), 11.32 (brs, 1H)

IR (KBr): 1719, 1717, 1681, 1593 cm$^{-1}$

EI-MS: m/e 329 (M$^+$)

Elemental analysis: for C$_{18}$H$_{27}$N$_5$O.0.5HCl.0.5H$_2$O

Calculated (%): C, 60.70; H, 7.92; N, 19.66 Found (%): C, 60.61; H, 8.24; N, 19.43

Example 8

Compound 10

Compound 10 was obtained from Compound 6a and (S)-valinol in the same manner as Example 1.

Yield: 61%

Melting point: 109–112° C. (toluene/cyclohexane)

Optical rotation: [α]$_D^{20}$–53.9° {c 1.00, CH$_3$OH, >99% ee [CHIRALCEL OD column (4.6×250 mm), Daicel Chemical Industries, elution solvent: hexane/ethanol/diethylamine=95/5/0.05]}

Elemental analysis: for C$_{18}$H$_{27}$N$_5$O.0.5HCl.H$_2$O

Calculated (%): C, 59.12; H, 8.13; N, 19.15 Found (%): C, 59.11; H, 8.29; N, 18.81

Example 9

Compound 11

Compound 11 was obtained from Compound 6a and (R)-leucinol in the same manner as Example 5.

Yield: 65%

Melting point: 221–223° C. (methanol/ether)

Optical purity: >99% ee [CHIRALCEL OD column (4.6×250 mm), Daicel Chemical Industries, elution solvent: hexane/ethanol/diethylamine=95/5/0.05]

$^1$H NMR (270 MHz, DMSO-$d_6$) δ: 0.87 (t, 3H, J=7.6 Hz), 0.91 (d, 3H, J=3.6Hz), 0.93 (d, 3H, J=4.3 Hz), 1.42 (m, 1H), 1.44–1.84 (m, 10H), 1.87–1.97 (m, 2H), 3.12 (quin, 1H, J=8.1 Hz), 3.56 (dd, 1H, J=10.9, 6.9 Hz), 3.87 (dd, 2H, J=7.9, 6.9 Hz), 4.12 (dd, 1H, J=10.9, 9.6 Hz), 4.24 (m, 1H), 4.25 (s, 2H)

IR (CHCl$_3$): 1716, 1682, 1581 cm$^{-1}$

EI-MS: m/e 343 (M$^+$)

Elemental analysis: for $C_{19}H_{29}N_5O.C_4H_6O_6.0.4H_2O$

Calculated (%): C, 55.17; H, 7.21; N, 13.99 Found (%): C, 55.23; H, 7.24; N, 13.87

Example 10

Compound 12

Compound 12 was obtained from Compound 6a and (S)-tert-leucinol in the same manner as Example 1.

Yield: 47%

Melting point: 184–186° C. (acetone/ether)

Optical rotation: $[α]_D^{24}$–33.3° {c 1.12, CHCl$_3$, >99% ee [CHIRALCEL OD column (4.6×250 mm), Daicel Chemical Industries, elution solvent: hexane/ethanol/diethylamine=95/5/0.05]}

$^1$H NMR (270 MHz, CDCl$_3$) δ: 0.99 (t, 3H, J=7.4 Hz), 1.06 (s, 9H), 1.65–1.95 (m, 8H), 2.10–2.2 (m, 2H), 3.28 (quin, 1H, J=7.9 Hz), 4.09 (m, 1H), 4.10 (t, 2H, J=7.6 Hz), 4.23 (m, 2H)

IR (CHCl$_3$): 1717, 1687, 1587 cm$^{-1}$

EI-MS: m/e 343 (M$^+$)

Elemental analysis: for $C_{19}H_{29}N_5O.HCl.0.5H_2O$

Calculated (%): C, 58.67; H, 8.03; N, 18.01 Found (%): C, 58.85; H, 8.17; N, 17.92

Example 11

Compound 13

Compound 13 was obtained from Compound 6a and 2-amino-1-hexanol in the same manner as Example 1.

Yield: 40%

Melting point: 146–148° C. (acetone)

$^1$H NMR (270 MHz, CDCl$_3$) δ: 0.94 (t, 3H, J=7.1 Hz), 0.98 (t, 3H, J=7.4 Hz), 1.36–1.45 (m, 2H), 1.61–1.92 (m, 12H), 2.08–2.21 (m, 2H), 3.27 (quin, 1H, J=7.9 Hz), 3.94 (m, 1H), 4.10 (t, 2H, J=7.4 Hz), 4.34–4.41 (m, 2H)

IR (CHCl$_3$): 1732, 1716, 1699, 1687, 1506 cm$^{-1}$

EI-MS: m/e 343 (M$^+$)

Elemental analysis: for $C_{19}H_{29}N_5O.1.2HCl$

Calculated (%): C, 58.93; H, 7.86; N, 18.09

Found (%): C, 59.2; H, 7.96; N, 18.13

Example 12

Compound 14

Compound 14 was obtained from Compound 6a and (S)-2-amino-3-cyclohexyl-1-propanol in the same manner as Example 1.

Yield: 36%

Melting point: 198–200° C. (acetone/ether)

Optical rotation: $[α]_D^{24}$–51.3° {c 0.60, CHCl$_3$, >99% ee [CHIRALCEL OD column (4.6×250 mm), Daicel Chemical Industries, elution solvent: hexane/ethanol/diethylamine=95/5/0.05]}

$^1$H NMR (270 MHz, CDCl$_3$) δ: 0.98 (t, 3H, J=7.4 Hz), 1.14–1.37 (m, 3H), 1.54–1.89 (m, 18H), 2.16 (m, 2H), 3.27 (quin, 1H, J=7.9 Hz), 3.91 (dd, 1H, J=11.2, 6.6 Hz), 4.10 (t, 2H, J=7.6 Hz), 4.38 (dd, 1H, J=11.2, 10.3 Hz), 4.48 (quin, 1H, J=6.6 Hz)

IR (CHCl$_3$): 1734, 1716, 1697, 1683, 1654, 1540 cm$^{-1}$

EI-MS: m/e 383 (M$^+$)

Elemental analysis: for $C_{22}H_{33}N_5O.HCl$

Calculated (%): C, 62.92; H, 8.16; N, 16.67 Found (%): C, 62.68; H, 8.21; N, 16.50

Example 13

Compound 15

Compound 15 was obtained from Compound 6a and (R)-phenylglycinol in the same manner as Example 1.

Yield: 49%

Melting point: 215–219° C. (chloroform/ether)

Optical rotation: $[α]_D^{20}$+87.5° {c 1.00, CH$_3$OH, >99% ee [CHIRALCEL OD column (4.6×250 mm), Daicel Chemical Industries, elution solvent: hexane/ethanol/diethylamine=95/5/0.05]}

$^1$H NMR (270 MHz, CDCl$_3$) δ: 1.00 (t, 3H, J=7.4 Hz), 1.65–2.00 (m, 8H), 2.10–2.25 (m, 2H), 3.20–3.35 (m, 1H), 4.12 (t, 2H, J=7.4 Hz), 4.18 (dd, 1H, J=11.5, 7.5 Hz), 4.72 (dd, 1H, J=11.5, 10.5 Hz), 5.54 (dd, 1H, J=10.0, 7.5 Hz), 7.25–7.45 (m, 5H)

IR (KBr): 1726, 1690, 1594 cm$^{-1}$

EI-MS: m/e 363 (M$^+$)

Elemental analysis: for $C_{21}H_{25}N_5O.HCl.0.2H_2O$

Calculated (%): C, 62.51; H, 6.59; N, 17.33 Found (%): C, 62.61; H, 6.99; N, 16.93

Example 14

Compound 16

Compound 16 was obtained from Compound 6a and (R)-phenylalaninol in the same manner as Example 1.

Yield: 43%

Melting point: 224–226° C. (toluene)

Optical rotation: $[α]_D^{20}$+47.3° {c 1.00, CH$_3$OH, >99% ee [CHIRALCEL OD column (4.6×250 mm), Daicel Chemical Industries, elution solvent: hexane/ethanol/diethylamine=95/5/0.05]}

$^1$H NMR (270 MHz, CDCl$_3$) δ: 0.95 (t, 3H, J=7.4 Hz), 1.65–2.00 (m, 8H), 2.15–2.30 (m, 2H), 3.00 (dd, 1H, J=14.0, 8.0 Hz), 3.23 (dd, 1H, J=14.0, 4.5 Hz), 3.25–3.40 (m, 1H), 4.00–4.15 (m, 3H), 4.21 (dd, 1H, J=9.0, 4.5 Hz), 4.65–4.75 (m, 1H), 7.20–7.40 (m, 5H)

IR (KBr): 1722, 1682, 1591 cm$^{-1}$

EI-MS: m/e 377 (M$^+$)

Elemental analysis: for $C_{22}H_{27}N_5O.HCl$

Calculated (%): C, 63.83; H, 6.82; N, 16.92 Found (%): C, 64.01; H, 6.88; N, 16.63

Example 15

Compound 17

Compound 17 was obtained from Compound 6a and (S)-phenylalaninol in the same manner as Example 1.

Yield: 71%

Melting point: 215–220° C. (ethanol)

Optical rotation: $[\alpha]_D^{20}$ −51.3° {c 1.00, $CH_3OH$, >99% ee [CHIRALCEL OD column (4.6×250 mm), Daicel Chemical Industries, elution solvent: hexane/ethanol/diethylamine= 95/5/0.05]}

Elemental analysis: for $C_{22}H_{27}N_5O \cdot HCl$

Calculated (%): C, 63.83; H, 6.82; N, 16.92 Found (%): C, 63.68; H, 7.14; N, 16.83

Example 16

Compound 18

Compound 18 was obtained from Compound 6a and 4-fluorophenylalaninol (Indian Journal of Chemistry, Section B, vol. 15B, p.260, 1977) in the same manner as Example 1.

Yield: 47%

Melting point: 226–228° C. (methanol/ether)

$^1$H NMR (270 MHz, $CDCl_3$) δ: 0.95 (t, 3H, J=7.4 Hz), 1.69–1.91 (m, 8H), 2.12–2.21 (m, 2H), 3.02 (dd, 1H, J=14.5, 7.2 Hz), 3.17 (dd, 1H, J=14.5, 4.0 Hz), 3.28 (quin, 1H, J=7.9 Hz), 4.05 (m, 1H), 4.06 (t, 2H, J=8.6 Hz), 4.24 (dd, 1H, J=11.9, 9.6 Hz), 4.67 (m, 1H), 7.03 (t, 2H, J=8.6 Hz), 7.25(t, 2H, J=8.6 Hz)

IR ($CHCl_3$) 1717, 1684, 1585, 1512 $cm^{-1}$

EI-MS: m/e 395 ($M^+$)

Elemental analysis: for $C_{22}H_{26}FN_5O \cdot HCl$

Calculated (%): C, 61.18; H, 6.30; N, 16.21 Found (%): C, 61.23; H, 6.38; N, 16.16

Example 17

Compound 19

Compound 19 was obtained from Compound 6a and 3-fluorophenylalaninol (Indian Journal of Chemistry, Section B, vol. 15B, p.260, 1977) in the same manner as Example 1.

Yield: 60%

Melting point: 171–173° C. (acetone/ether)

$^1$H NMR (270 MHz, $CDCl_3$) δ: 0.96 (t, 3H, J=7.4 Hz), 1.63–1.94 (m, 8H), 2.08–2.23 (m, 2H), 2.99 (dd, 1H, J=14.2, 7.6 Hz), 3.22–3.33 (m, 2H), 4.06 (m, 1H), 4.07 (t, 2H, J=6.3 Hz), 4.24 (dd, 1H, J=11.9, 9.9 Hz), 4.69 (m, 1H), 6.95–7.08 (m, 3H), 7.31 (m, 1H)

IR ($CHCl_3$): 1716, 1682, 1585 $cm^{-1}$

EI-MS: m/e 395 ($M^+$)

Elemental analysis: for $C_{22}H_{26}FN_5O \cdot HCl$

Calculated (%): C, 61.18; H, 6.30; N, 16.21 Found (%): C, 61.03; H, 6.34; N, 16.01

Example 18

Compound 20

Compound 20 was obtained from Compound 6a and 4-chlorophenylalaninol (DE-A-2206961) in the same manner as Example 1.

Yield: 52%

Melting point: 222–224° C. (acetone)

$^1$H NMR (270 MHz, $CDCl_3$) δ: 0.95 (t, 3H, J=7.3 Hz), 1.64–1.92 (m, 8H), 2.05–2.21 (m, 2H), 3.01 (dd, 1H, J=13.9, 6.9 Hz), 3.16 (dd, 1H, J=13.9, 4.6 Hz), 3.28 (quin, 1H, J=7.9 Hz), 4.03 (dd, 1H, J=11.9, 6.6 Hz), 4.06 (t, 2H, J=7.3 Hz), 4.24 (dd, 1H, J=11.9, 9.9 Hz), 4.66 (m, 1H), 7.2 (d, 2H, J=8.3 Hz), 7.31 (d, 2H, J=8.3 Hz)

IR ($CHCl_3$): 1714, 1682, 1585 $cm^{-1}$

EI-MS: m/e 411 ($M^+$)

Elemental analysis: for $C_{22}H_{26}ClN_5O \cdot HCl$

Calculated (%): C, 58.93; H, 6.07; N, 15.62 Found (%): C, 58.98; H, 6.12; N, 15.45

Example 19

Compound 21

Compound 21 was obtained from Compound 6a and 3-chlorophenylalaninol (DE-A-2206961) in the same manner as Example 1.

Yield: 32%

Melting point: 146–148° C. (acetone)

$^1$H NMR (270 MHz, $CDCl_3$) δ: 0.96 (t, 3H, J=7.6 Hz), 1.69–1.90 (m, 8H), 2.15 (m, 2H), 2.98 (dd, 1H, J=14.1, 7.6 Hz), 3.20 (dd, 1H, J=14.1, 5.0 Hz), 3.28 (quin, 1H, J=7.9 Hz), 4.03 (dd, 1H, J=9.9, 6.3 Hz), 4.07 (t, 2H, J=6.3 Hz), 4.24 (dd, 1H, J=11.4, 9.9 Hz), 4.67 (m, 1H), 7.17–7.33 (m, 4H)

IR ($CHCl_3$): 1717, 1682, 1585 $cm^{-1}$

EI-MS: m/e 411 ($M^+$)

Elemental analysis: for $C_{22}H_{26}ClN_5O \cdot 0.9HCl \cdot H_2O$

Calculated (%): C, 57.10; H, 6.29; N, 15.13 Found (%): C, 57.01; H, 6.29; N, 15.11

Example 20

Compound 22

Compound 22 was obtained from Compounds 6a and 2,6-dichlorophenylalaninol (DE-A-2206961) in the same manner as Example 1.

Yield: 52%

Melting point: 203–205° C. (acetone/ether)

$^1$H NMR (270 MHz, $CDCl_3$) δ: 0.99 (t, 3H, J=7.6 Hz), 1.65–1.86 (m, 8H), 2.15 (m, 2H), 3.27 (quin, 1H, J=7.9 Hz), 3.45 (dd, 1H, J=13.8, 8.0 Hz), 3.54 (dd, 1H, J=13.8, 6.8 Hz), 4.12 (t, 2H, J=7.6 Hz), 4.21 (d, 2H, J=7.9 Hz), 4.88 (quin, 1H, J=7.9 Hz), 7.23 (d, 1H, J=8.9 Hz), 7.40 (d, 2H, J=8.6 Hz)

IR ($CHCl_3$): 1715, 1682, 1585 $cm^{-1}$

EI-MS: m/e 445 ($M^+$)

Elemental analysis: for $C_{22}H_{25}Cl_2N_5O \cdot HCl$

Calculated (%): C, 54.73; H, 5.43; N, 14.50 Found (%): C, 54.68; H, 5.46; N, 14.28

Example 21

Compound 23

Compound 23 was obtained from Compound 6a and 4-bromophenylalaninol (Journal of Medicinal Chemistry, vol. 26 volumes, p.1556, 1983) in the same manner as Example 1.

Yield: 35%

Melting point: 184–186° C. (acetone)

$^1$H NMR (270 MHz, $CDCl_3$) δ: 0.95 (t, 3H, J=7.4 Hz), 1.64–1.95 (m, 8H), 2.08–2.24 (m, 2H), 2.99 (dd, 1H, J=13.9, 7.6 Hz), 3.15 (dd, 1H, J=13.9, 4.6 Hz), 3.25 (m, 1H), 3.99–4.11 (m, 3H), 4.24 (m, 1H), 4.70 (m, 1H), 7.14–7.48 (m, 4H)

IR (CHCl$_3$): 1717, 1682, 1585 cm$^{-1}$
EI-MS: m/e 455 (M$^+$)
Elemental analysis: for C$_{22}$H$_{26}$BrN$_5$O.HCl
Calculated (%): C, 53.62; H, 5.52; N, 14.21 Found (%): C, 53.43; H, 5.53; N, 13.95

Example 22

Compound 24

Compound 24 was obtained from Compound 6a and 3-bromophenylalaninol (Journal of Medicinal Chemistry, vol. 26, p.1556, 1983) in the same manner as Example 1.

Yield: 12%
Melting point: 104–106° C. (acetone/ether)
$^1$H NMR (270 MHz, CDCl$_3$) δ: 0.96 (t, 3H, J=7.4 Hz), 1.64–1.96 (m, 8H), 2.15 (m, 2H), 2.97 (dd, 1H, J=13.9, 7.6 Hz), 3.19 (dd, 1H, J=13.9, 6.2 Hz), 3.28 (quin, 1H, J=7.9 Hz), 4.03 (dd, 1H, J=11.8, 9.5 Hz), 4.07 (t, 2H, J=5.9 Hz), 4.23 (dd, 1H, J=12.2, 9.5 Hz), 4.68 (m, 1H), 7.21–7.26 (m, 3H), 7.42 (m, 1H)
IR (CHCl$_3$): 1716, 1682, 1585 cm$^{-1}$
EI-MS: m/e 455 (M$^+$).

Example 23

Compound 25

Compound 25 was obtained from Compound 6a and 4-methoxyphenylalaninol (Tetrahedron Letters, vol. 30, p.4211, 1989) in the same manner as Example 1.

Yield: 36%
Melting point: 168–170° C. (acetone/ether)
$^1$H NMR (270 MHz, CDCl$_3$) δ: 0.95 (t, 3H, J=7.4 Hz), 1.62–1.98 (m, 8H), 2.14–2.23 (m, 2H), 2.98 (dd, 1H, J=11.8, 7.6 Hz), 3.14 (dd, 1H, J=11.8, 4.5 Hz), 3.28 (quin, 1H, J=7.8 Hz), 3.77 (s, 3H), 4.05 (t, 2H, J=8.5 Hz), 4.06 (m, 1H), 4.20 (m, 1H), 4.67 (m, 1H), 6.85 (d, 2H, J=7.7 Hz), 7.19 (d, 2H, J=7.7 Hz)
IR (CHCl$_3$): 1716, 1682, 1585, 1514 cm$^{-1}$
EI-MS: m/e 407 (M$^+$)
Elemental analysis: for C$_{23}$H$_{29}$N$_5$O$_2$.HCl
Calculated (%): C, 62.22; H, 6.81; N, 15.77 Found (%): C, 62.38; H, 7.02; N, 15.67

Example 24

Compound 26

Compound 26 was obtained from Compound 6a and 4-nitrophenylalaninol (Journal of Chemical Society Perkin Transaction I, p.867, 1989) in the same manner as Example 1.

Yield: 6%
Melting point: 215–217° C. (acetone)
$^1$H NMR (270 MHz, CDCl$_3$) δ: 0.95 (t, 3H, J=7.4 Hz), 1.62–1.93 (m, 8H), 2.04–2.11 (m, 2H), 3.21–3.38 (m, 3H), 3.98–4.14 (m, 3H), 4.35 (m, 1H), 4.78 (m, 1H), 7.46–7.54 (m, 2H), 8.20–8.25 (m, 2H)
IR (CHCl$_3$): 1716, 1689, 1587, 1525, 1506 cm$^{-1}$
EI-MS: m/e 422 (M$^+$)
Elemental analysis: for C$_{22}$H$_{26}$N$_6$O$_3$.HCl
Calculated (%): C, 57.58; H, 5.93; N, 18.31 Found (%): C, 57.34; H, 5.91; N, 17.95

Example 25

Compound 27

Compound 27 was obtained from Compound 6a and (R)-O-benzyltyrosinol (Journal of Organic Chemistry, vol. 56, p.1961, 1991) in the same manner as Example 1.

Yield: 28%
Melting point: 202–204° C. (acetone/ether)
Optical rotation: [α]$_D^{24}$–34.5° {c 1.00, CDCl$_3$, >99% ee [CHIRALCEL OD column (4.6×250 mm), Daicel Chemical Industries, elution solvent: hexane/ethanol/diethylamine= 95/5/0.05]}
$^1$H NMR (270 MHz, CDCl$_3$) δ: 0.95 (t, 3H, J=7.4 Hz), 1.62–1.98 (m, 8H), 2.15 (m, 2H), 2.95 (dd, 1H, J=13.8, 7.6 Hz), 3.15 (dd, 1H, J=13.8, 4.3 Hz), 3.28 (quin, 1H, J=7.6 Hz), 4.06 (m, 3H), 4.20 (dd, 1H, J=11.9, 9.5 Hz), 4.65 (m, 1H), 5.02 (s, 2H), 6.93 (d, 2H, J=8.6 Hz), 7.18 (d, 2H, J=8.6 Hz), 7.34–7.41 (m, 5H)
IR (CHCl$_3$): 1714, 1687, 1682, 1587, 1511 cm$^{-1}$
EI-MS: m/e 482 (M$^+$–H)
Elemental analysis: for C$_{29}$H$_{33}$N$_5$O$_2$.1.1HCl
Calculated (%): C, 66.51; H, 6.56; N, 13.37 Found (%): C, 66.60; H, 6.60; N, 13.26

Example 26

Compound 28

Compound 28 was obtained from Compound 6a and (S)-O-benzyltyrosinol (Journal of Organic Chemistry, vol. 56, p.1961, 1991) in the same manner as Example 1.

Yield: 47%
Melting point: 195–197° C. (acetone/ether)
Optical rotation: [α]$_D^{24}$31.4° {c 0.72, CDCl$_3$, >99% ee [CHIRALCEL OD column (4.6×250 mm), Daicel Chemical Industries, elution solvent: hexane/ethanol/diethylamine= 95/5/0.05]}
$^1$H NMR (270 MHz, CDCl$_3$) δ: 0.95 (t, 3H, J=7.5 Hz), 1.72–1.88 (m, 8H), 2.15 (m, 2H), 2.95 (dd, 1H, J=13.9, 7.6 Hz), 3.15 (dd, 1H, J=13.9, 4.6 Hz), 3.27 (quin, 1H, J=7.6 Hz), 4.06 (t, 2H, J=7.6 Hz), 4.07 (dd, 1H, J=9.9, 2.0 Hz), 4.21 (dd, 1H, J=11.8, 9.9 Hz), 4.65 (m, 1H), 5.02 (s, 2H), 6.93 (d, 2H, J=8.6 Hz), 7.18 (d, 2H, J=8.9 Hz), 7.32–7.43 (m, 5H)
IR (CHCl$_3$): 1716, 1684, 1587, 1512 cm$^{-1}$
EI-MS: m/e 499 (M$^+$)
Elemental analysis: for C$_{29}$H$_{33}$N$_5$O$_3$.0.6 HCl
Calculated (%): C, 66.79; H, 6.49; N, 13.43 Found (%): C, 66.61; H, 6.63; N, 13.31

Example 27

Compound 29

Compound 29 was obtained from 8-cyclopentyl-7-methyl-6-methylthio-3-propyl-7H-purin-2(3H)-one (Compound 29a, EP-A-423805) and (R)-phenylalaninol in the same manner as Example 1.

Yield: 12%
Melting point: 142–144° C. (ethyl acetate/hexane) Optical purity: >99% ee [CHIRALCEL OD column (4.6×250 mm), Daicel Chemical Industries, elution solvent: hexane/ ethanol/diethylamine =95/5/0.05]
$^1$H NMR (270 MHz, CDCl$_3$) δ: 0.93 (t, 3H, J=7.4 Hz), 1.71 (quin, 2H, J=7.3 Hz), 1.81–2.07 (m, 8H), 2.68 (dd, 1H, J=13.5, 8.9 Hz), 3.10 (quin, 1H, J=7.9 Hz), 3.20 (dd, 1H, J=13.5, 5.0 Hz), 3.63 (dd, 1H, J=10.9, 6.6 Hz), 3.78 (dd, 1H, J=10.9, 9.6 Hz), 3.88 (s, 3H), 3.91 (t, 2H, J=7.3 Hz), 4.51 (m, 1H), 7.18–7.33 (m, 5H)
IR (CHCl$_3$): 1717, 1684, 1653, 1439 cm$^{-1}$
EI-MS: m/e 391 (M$^+$).

Example 28

Compound 30

Compound 30 was obtained from Compound 6a and 2-amino-3,3-diphenyl-1-propanol(Journal of Organic Chemistry, vol. 52, p.1487, 1987) in the same manner as Example 1.

Yield: 15%

Melting point: 178–180° C. (ethyl acetate/ether)

$^1$H NMR (270 MHz, CDCl$_3$) δ: 0.91 (t, 3H, J=7.4 Hz), 1.61–1.97 (m, 8H), 2.18 (m, 2H), 3.27 (quin, 1H, J=7.9 Hz), 3.76 (d, 1H, J=9.9 Hz), 3.97 (dd, 1H, J=11.9, 9.9 Hz), 4.18 (t, 2H, J=7.4 Hz), 4.55 (d, 1H, J=11.2 Hz), 5.21 (q, 1H, J=10.5 Hz), 7.10–7.40 (m, 6H), 7.50–7.56 (m 4H)

IR (CHCl$_3$): 1715, 1684, 1678, 1599, 1514 cm$^{-1}$

EI-MS: m/e 453 (M$^+$)

Elemental analysis: for C$_{28}$H$_{31}$N$_5$O.2.1HCl

Calculated (%): C, 63.44; H, 6.29; N, 13.21 Found (%): C, 63.58; H, 6.38; N, 13.04

Example 29

Compound 31

Compound 31 was obtained from Compound 6a and 2-amino-4-phenyl-1-butanol (Tetrahedron Letters, vol. 24, p.2935, 1983) in the same manner as Example 1.

Yield: 17%

Melting point: 171–173° C. (acetone/ether)

$^1$H NMR (270 MHz, CDCl$_3$) δ: 0.95 (t, 3H, J=7.4 Hz), 1.62–1.92 (m, 8H), 1.97–2.23 (m, 4H), 2.79 (t, 1H, J=11.6 Hz), 2.81 (t, 1H, J=11.6 Hz), 3.2 (m, 1H), 3.85 (m, 1H), 4.02 (t, 2H, J=7.4 Hz), 4.27 (m, 2H), 7.20–7.38 (m, 5H)

IR (CHCl$_3$): 1716, 1682, 1586 cm$^{-1}$

EI-MS: m/e 391 (M$^+$)

Elemental analysis: for C$_{23}$H$_{29}$N$_5$O.1.4HCl

Calculated (%): C, 62.42; H, 6.92; N, 15.82 Found (%): C, 62.40; H, 6.99; N, 15.71

Example 30

Compound 32

3-Benzyl-8-cyclopentyl-6-methylthio-7H-purin-2(3H)-one (Compound 32a) was obtained by a known method (Journal of Chemical Society Perkin I, p.739, 1973).

$^1$H NMR (270 MHz, DMSO-d$_6$) δ: 1.55–2.07 (m, 8H), 2.56 (s, 3H), 3.19 (quin, 1H, J=7.9 Hz), 5.19 (s, 2H), 7.21–7.34 (m, 5H), 13.10 (brs, 1H).

Compound 32 was obtained from Compound 32a and (R)-phenylalaninol in the same manner as Example 1.

Yield: 51%

Melting point: 237–239° C. (ethyl acetate/ether)

Optical rotation: [α]$_D^{24}$–18.4° {c 0.93, CHCl$_3$, >99% ee [CHIRALCEL OD column (4.6×250 mm), Daicel Chemical Industries, elution solvent: hexane/ethanol/diethylamine=95/5/0.05]}

$^1$ HNMR (270 MHz, CDCl$_3$) δ: 1.65–2.23 (m, 8H), 2.96 (dd, 1H, J=13.6, 7.6 Hz), 3.21 (dd, 1H, J=13.6, 4.3 Hz), 3.31 (quin, 1H, J=7.7 Hz), 4.05 (dd, 1H, J=9.9, 6.6 Hz), 4.18 (dd, 1H, J=11.9, 9.9 Hz), 4.67 (m, 1H), 5.24 (s, 2H), 7.24–7.34 (m, 8H), 7.46–7.50 (m, 2H)

IR (CHCl$_3$): 1716, 1684, 1583 cm$^{-1}$

EI-MS: m/e 425 (M$^+$)

Elemental analysis: for C$_{26}$H$_{27}$N$_5$O.0.9HCl

Calculated (%): C, 68.13; H, 6.14; N, 15.28 Found (%): C, 68.16; H, 6.23; N, 15.19

Example 31

Compound 33

Compound 33 was obtained from 6-methylthio-3-propyl-7H-purin-2(3H)-one (EP-A-423805, Compound 33a) and (R)-phenylalaninol in the same manner as Example 1.

Yield: 72%

Melting point: 234–236° C. (acetone/ether)

Optical purity: >99% ee [CHIRALCEL OD column (4.6×250 mm), Daicel Chemical Industries, elution solvent: hexane/ethanol/diethylamine=95/5/0.05]]

$^1$H NMR (270 MHz, CDCl$_3$) δ: 0.96 (t, 3H, J=7.6 Hz), 1.76 (q, 2H, J=7.5 Hz), 3.07 (dd, 1H, J=10.6, 7.4 Hz), 3.23 (dd, 1H, J=10.8, 4.2 Hz), 4.09 (t, 2H, J=7.4 Hz), 4.13 (dd, 1H, J=9.8, 7.3 Hz), 4.22 (dd, 1H, J=11.8, 9.9 Hz), 4.75 (m, 1H), 7.21–7.36 (m, 5H), 7.94 (s, 1H)

IR (CHCl$_3$): 1717, 1684, 1587 cm$^{-1}$

EI-MS: m/e 309 (M$^+$)

Elemental analysis: for C$_{17}$H$_{19}$N$_5$O.2.1HCl

Calculated (%): C, 52.91; H, 5.51; N, 18.15 Found (%): C, 53.08; H, 5.41; N, 18.26

Example 32

Compound 34

Compound 33a (5.00 g, 2.3 mmol) was treated with benzyl bromide (2.9 mL) in the presence of sodium hydride (60% in oil, 1.78 g, 44.5 mmol, 2.0 eq.) in N,N-dimethylformamide (250 ml) to obtain 5.84 g (83%) of 7-benzyl-6-methylthio-3-propyl-7H-purin-2(3H)-one (Compound 34a).

$^1$H NMR (270 MHz, DMSO-d$_6$) δ: 0.89 (t, 3H, J=7.3 Hz), 1.70 (q, 2H, J=7.3 Hz), 2.50 (s, 3H), 4.01 (t, 2H, J=7.6 Hz), 5.60 (s, 2H), 7.16 (d, 2H, J=6.6 Hz), 7.24–7.39 (m, 3H), 8.39 (s, 1H)

Compound 34 was obtained from Compound 34a and (R)-phenylalaninol in the same manner as Example 1.

Yield: 47%

Melting point: 198–200° C. (ethyl acetate/ether)

Optical rotation: [α]$_D^{20}$–15.7° {c 0.64, CHCl$_3$, >99% ee [CHIRALCEL OD column (4.6×250 mm), Daicel Chemical Industries, elution solvent: hexane/ethanol/diethylamine=95/5/0.05]}

$^1$H NMR (270 MHz, CDCl$_3$) δ: 0.94 (t, 3H, J=7.6 Hz), 1.72 (quin, 2H, J=7.6 Hz), 3.17 (dd, 1H, J=13.9, 7.6 Hz), 3.38 (dd, 1H, J=13.9, 3.2 Hz), 4.00 (dd, 1H, J=11.6, 6.9 Hz), 4.02 (t, 2H, J=6.9 Hz), 4.12 (dd, 1H, J=11.6, 10.2 Hz), 4.88 (m, 1H), 6.00 (d, 1H, J=15.4 Hz), 6.20 (d, 1H, J=15.4 Hz), 7.16–7.20 (m, 5H), 7.33–7.48 (m, 5H), 7.85 (s, 1H)

IR (CHCl$_3$): 1716, 1713, 1664, 1579 cm$^{-1}$

EI-MS: m/e 399 (M$^+$)

Elemental analysis: for C$_{24}$H$_{25}$N$_5$O.HCl

Calculated (%): C, 66.12; H, 6.01; N, 16.06 Found (%): C, 66.13; H, 6.08; N, 16.00

Example 33

Compound 35

To a solution of 3,8-dipropylxanthine (18.0 g, 76.27 mmol) obtained by a known method (EP-A-038,784) in pyridine (300 mL) was added diphosphorus pentasulfide (35.0 g, 157.66 mmol, 2.0 eq.) and the mixture was heated at 130° C. for 2 hours with stirring. The reaction solution was poured into ice water and the mixture was extracted with chloroform. The organic layer was washed with a saturated aqueous solution of sodium chloride and dried, and then the solvent was evaporated. The residue was purified by silica gel column chromatography (chloroform:methanol= 20:1) to obtain a thione derivative (5.4 g, 28%). The thione derivative (5.4 g, 21.43 mmol) was dissolved in a mixture of a 0.5 mol/L aqueous solution of sodium hydroxide (75 mL) and ethanol (30 mL) and the mixture was stirred at room temperature for 30 minutes. To the mixture was added methyl iodide (2 mL) and the mixture was stirred at room temperature for 1 hour. The reaction solution was neutralized with a 2 mol/L solution of hydrochloric acid, and the precipitated crystals were collected by filtration to obtain 6-methylthio-3,8-dipropyl-7H-purin-2(3H)-one (Compound 35a, 3.2 g, 56%).

$^1$H NMR (270 MHz, CDCl$_3$) δ: 0.98 (t, 3H, J=7.3 Hz), 1.02 (t, 3H, J=7.3 Hz), 1.78–1.93 (m, 4H), 2.50 (s, 3H), 2.89 (t, 2H, J=7.3 Hz), 4.22 (t, 2H, J=7.6 Hz)

Compound 35 was obtained from Compound 35a and (R)-phenylalaninol in the same manner as Example 1.

Yield: 29%

Melting point: 195–197° C. (acetone/ether)

Optical rotation: $[\alpha]_D^{24}$-13.6° {c 0.63, CHCl$_3$, >99% ee [CHIRALCEL OD column (4.6×250 mm), Daicel Chemical Industries, elution solvent: hexane/ethanol/diethylamine= 95/5/0.05]}

$^1$NMR (270 MHz, CDCl$_3$) δ: 0.95 (t, 3H, J=7.6 Hz), 1.03 (t, 3H, J=6.6 Hz), 1.76 (q, 2H, J=7.9 Hz), 1.86 (q, 2H, J=6.9 Hz), 2.84 (dd, 2H, J=8.6, 7.9 Hz), 3.00 (dd, 1H, J=13.9, 7.6 Hz), 3.23 (dd, 1H, J=13.9, 3.6 Hz), 4.05 (t, 2H, J=7.9 Hz), 4.06 (m, 1H), 4.21 (t, 1H, J=10.9 Hz), 4.70 (m, 1H), 7.23–7.36 (m, 5H)

IR (CHCl$_3$): 1716, 1506 cm$^{-1}$

EI-MS: m/e 351 (M$^+$)

Elemental analysis: for C$_{20}$H$_{25}$N$_5$O.1.1HCl

Calculated (%): C, 61.35; H, 6.72; N, 17.89 Found (%): C, 61.39; H, 6.80; N, 17.79

Example 34

Compound 36

By using 8-cyclopropyl-3-propylxanthine obtained by a known method (EP-A-256,692), the 6-methylthio derivative (Compound 36a) was obtained in the same manner as Example 33.

$^1$H NMR (270 MHz, DMSO-d$_6$) δ: 0.85 (t, 3H, J=7.2 Hz), 1.00–1.16 (m, 4H), 1.65 (q, 2H, J=7.2 Hz), 2.06 (m, 1H), 2.55 (s, 3H), 3.92 (t, 2H, J=6.9 Hz)

Compound 36 was obtained from Compound 36a and (R)-phenylalaninol in the same manner as Example 1.

Yield: 26%

Melting point: 187–189° C. (acetone/ether)

Optical purity: >99% ee [CHIRALCEL OD column (4.6× 250 mm), Daicel Chemical Industries, elution solvent: hexane/ethanol/diethylamine=95/5/0.05)]

$^1$H NMR (270 MHz, CDCl$_3$) δ: 0.93 (t, 3H, J=7.3 Hz), 1.22 (d, 4H, J=6.6 Hz), 1.71 (quin, 2H, J=7.3 Hz), 2.12 (quin, 1H, J=6.6 Hz), 3.00 (dd, 1H, J=13.8, 7.6 Hz), 3.22 (dd, 1H, J=13.8, 4.6 Hz), 4.01 (t, 2H, J=7.6 Hz), 4.06 (dd, 1H, J=11.8, 6.2 Hz), 4.20 (dd, 1H, J=11.8, 9.5 Hz), 4.68 (m, 1H), 7.24–7.37 (m, 5H)

IR (CHCl$_3$): 1717, 1682, 1585 cm$^{-1}$

EI-MS: m/e 349 (M$^+$)

Example 35

Compound 37

By using 8-cyclobutyl-3-propyl-6-thioxanthine obtained by a known method (EP-A-256,692), the 6-methylthio derivative (Compound 37a) was obtained in the same manner as Example 33.

$^1$H NMR (270 MHz, DMSO-d$_6$) δ: 0.88 (t, 3H, J=7.2 Hz), 1.68 (q, 2H, J=6.9 Hz), 1.81–2.10 (m, 2H), 2.21–2.43 (m, 4H), 2.56 (s, 3H), 3.64 (quin, 1H, J=8.9 Hz), 3.97 (t, 2H, J=7.4 Hz)

Compound 37 was obtained from Compound 37a and (R)-phenylalaninol in the same manner as Example 1.

Yield: 26%

Melting point: 214–216° C. (acetone/ether)

Optical rotation: $[\alpha]_D^{24}$-25.6° {c 1.07, CHCl$_3$, >99% ee [CHIRALCEL OD column (4.6×250 mm), Daicel Chemical Industries, elution solvent: hexane/ethanol/diethylamine= 95/5/0.05]}

$^1$H NMR (270 MHz, CDCl$_3$) δ: 0.96 (t, 3H, J=7.6 Hz), 1.75 (quin, 2H, J=7.6 Hz), 2.03–2.16 (m, 2H), 2.43 (dt, 4H, J=8.6, 6.6 Hz), 3.01 (dd, 1H, J=13.8, 7.6 Hz), 3.23 (dd, 1H, J=13.6, 4.6 Hz), 3.72 (quin, 1H, J=8.6 Hz), 4.06 (dd, 1H, J=11.9, 2.9 Hz), 4.09 (t, 2H, J=7.5 Hz), 4.22 (dd, 1H, J=11.9, 9.6 Hz), 4.70 (m, 1H), 7.24–7.37 (m, 5H)

IR (CHCl$_3$): 1716, 1684, 1587 cm$^{-1}$

EI-MS: m/e 361 (M$^+$)

Elemental analysis: for C$_{21}$H$_{25}$N$_5$O.0.7HCl.0.7H$_2$O

Calculated (%): C, 62.81; H, 6.80; N, 17.44 Found (%): C, 62.67; H, 6.80; N, 17.40

Example 36

Compound 38

By using 8-cyclohexyl-3-propylxanthine obtained by a known method (Journal of Medicinal Chemistry, vol. 32, p.1231, 1989), the 6-methylthio derivative (Compound 38a) was obtained in the same manner as Example 33.

$^1$H NMR (270 MHz, CDCl$_3$) δ: 0.97 (t, 3H, J=7.2 Hz), 1.23–1.48 (m, 4H), 1.58–1.96 (m, 6H), 2.01 (s, 3H), 2.06 (d, 2H, J=8.2 Hz), 2.87 (m, 1H), 4.25 (t, 2H, J=7.2 Hz), 13.08 (brs, 1H)

Compound 38 was obtained from Compound 38a and (R)-phenylalaninol in the same manner as Example 1.

Yield: 28%

Melting point: 243–245° C. (acetone/ether)

Optical rotation: $[\alpha]_D^{24}$-28.2° {c 1.09, CHCl$_3$, >99% ee [CHIRALCEL OD column (4.6×250 mm), Daicel Chemical Industries, elution solvent: hexane/ethanol/diethylamine= 95/5/0.05]}

$^1$H NMR (270 MHz, CDCl$_3$) δ: 0.95 (t, 3H, J=7.3 Hz), 1.28–1.90 (m, 10H), 2.13 (brd, 2H, J=13.6 Hz), 2.87 (tt, 1H, J=11.4, 3.5 Hz), 3.00 (dd, 1H, J=13.8, 7.9 Hz), 3.24 (dd, 1H, J=13.8, 4.6 Hz), 4.05 (dd, 1H, J=11.9, 3.3 Hz), 4.08 (t, 2H, J=6.3 Hz), 4.21 (dd, 1H, J=11.9, 9.6 Hz), 4.70 (m, 1H), 7.21–7.37 (m, 5H)

IR (CHCl$_3$) 1714, 1636, 1682, 1585 cm$^{-1}$

EI-MS: m/e 391 (M$^+$)

Elemental analysis: for C$_{23}$H$_{29}$N$_5$O.HCl

Calculated (%): C, 64.55; H, 7.07; N, 16.36 Found (%): C, 64.42; H, 7.10; N, 16.19

Example 37

Compound 39

Compound 39 was obtained from Compound 3a and (R)-phenylalaninol in the same manner as Example 1.

Yield: 35%

Melting point: 232–234° C. (acetone/ether)

Optical rotation: $[\alpha]_D^{24}$ −41.4° {c 0.41, CHCl$_3$, >99% ee [CHIRALCEL OD column (4.6×250 mm), Daicel Chemical Industries, elution solvent: hexane/ethanol/diethylamine= 95/5/0.05]}

$^1$H NMR (270 MHz, CDCl$_3$) δ: 0.98 (t, 3H, J=7.4 Hz), 1.61–2.45 (m, 14H), 2.69 (dd, 1H, J=11.7, 7.3 Hz), 2.97 (quin, 1H, J=7.2 Hz), 3.21 (dd, 1H, J=11.7, 4.5 Hz), 4.07 (dd, 1H, J=11.0, 3.3 Hz), 4.08 (t, 2H, J=6.9 Hz), 4.20 (t, 1H, J=9.6 Hz), 4.66 (m, 1H), 7.23–7.39 (m, 5H)

IR (CHCl$_3$): 1714, 1693, 1682, 1585 cm$^{-1}$

EI-MS: m/e 429 (M$^+$)

Elemental analysis: for C$_{26}$H$_{31}$N$_5$O.0.3HCl.1.5H$_2$O

Calculated (%): C, 66.80; H, 7.39; N, 14.98 Found (%): C, 66.84; H, 7.09; N, 15.02

Example 38

Compound 40

By using 8-cyclopentylmethyl-3-propylxanthine obtained by a known method (Journal of Medicinal Chemistry, vol. 36, p.2508, 1993), the 6-methylthio derivative (Compound 40a) was obtained in the same manner as Example 33.

Compound 40 was obtained from Compound 40a and (R)-phenylalaninol in the same manner as Example 1.

Yield: 87%

Melting point: 211–213° C. (acetone/ether)

$^1$H NMR (270 MHz, CDCl$_3$) δ: 0.95 (t, 3H, J=7.4 Hz), 1.21–1.29 (m, 2H), 1.54–1.89 (m, 9H), 2.87 (d, 2H, J=7.6 Hz), 3.02 (dd, 1H, J=14.0, 7.8 Hz), 3.04 (dd, 1H, J=14.0, 4.6 Hz), 4.05 (t, 2H, J=7.1 Hz), 4.09 (dd, 1H, J=11.6, 6.6 Hz), 4.21 (t, 1H, J=9.9 Hz), 4.69 (m, 1H), 7.24–7.36 (m, 5H)

IR (KBr): 1722, 1686, 1676, 1592 cm$^{-1}$

EI-MS: m/e 391 (M$^+$)

Elemental analysis: for C$_{23}$H$_{29}$N$_5$O.HCl.0.2H$_2$O

Calculated (%): C, 64.01; H, 7.10; N, 16.23 Found (%): C, 63.93; H, 7.23; N, 16.56

Example 39

Compound 41

By using 8-isopropyl-3-propylxanthine obtained by a known method (EP-A-038,784), the 6-methylthio derivative (Compound 41a) was obtained in the same manner as Example 33.

Compound 41 was obtained from Compound 41a and (R)-phenylalaninol in the same manner as Example 1.

Yield: 48%

Melting point: 169–170° C. (acetone/ether)

Optical rotation: $[\alpha]_D^{25}$ −17.0° (c 1.15, CHCl$_3$, >99% ee [CHIRALCEL OD column (4.6×250 mm), Daicel Chemical Industries, elution solvent: ethanol]

$^1$H NMR (270 MHz, CDCl$_3$) δ: 0.95 (t, 3H, J=7.4 Hz), 1.42 (d, 6H, J=6.9 Hz), 1.77 (q, 2H, J=7.4 Hz), 3.00 (dd, 1H, J=13.9, 7.6 Hz), 3.20 (q, 1H, J=6.9 Hz), 3.21 (dd, 1H, J=13.8, 4.6 Hz), 4.07 (t, 2H, J=7.6 Hz), 4.08 (dd, 1H, J=12.2, 5.6 Hz), 4.21 (dd, 1H, J=11.9, 9.9 Hz), 4.70 (m, 1H), 7.25–7.34 (m, 5H), 11.44 (s, 1H), 13.57 (s, 1H)

IR (KBr): 1729, 1711, 1693, 1678, 1656, 1592, 1540 cm$^{-1}$

EI-MS: m/e 351 (M$^+$)

Elemental analysis: for C$_{20}$H$_{25}$N$_5$O.HCl

Calculated (%): C, 61.93; H, 6.76; N, 18.05 Found (%): C, 62.14; H, 6.79; N, 18.09

Example 40

Compound 42

5,6-Diamino-1,2-dihydro-4-mercapto-2-oxo-1-propylpyrimidine (Compound 42a, 1.00 g, 4.99 mmol) obtained by a known method (Journal of Organic Chemistry, vol. 25, p.1752, 1960) was suspended in a mixed solvent of dioxane (12 mL) and water (6 mL). To the suspension was added 3-furancarboxylic acid (0.56 g, 4.99 mmol) and 1-ethyl-3-[3-(dimethylamino)propyl]carbodiimide hydrochloride (1.63 g, 8.50 mmol) and the mixture was stirred at room temperature for 24 hours. To the reaction mixture was added a 2 mol/L aqueous solution of sodium hydroxide (50 mL), and the mixture was stirred under reflux by heating for 2.5 hours. The mixture was adjusted to pH 6.5 with 4 mol/L hydrochloric acid, and the precipitated solid was collected by filtration. The solid obtained was dissolved in a 0.5 mol/L aqueous solution of sodium hydroxide (7.0 mL). To the solution was added methyl iodide (0.4 mL) and the mixture was stirred at room temperature for 4 hours. The reaction mixture was adjusted to pH 7 with 4 mol/L hydrochloric acid, and the resulting solid was separated by filtration and dried under reduced pressure to obtain the 6-methylthio derivative (Compound 42b, 870 mg, 60%). A mixture of Compound 42b (0.30 g, 1.03 mmol) and (R)-phenylalaninol (0.24 g, 1.55 mmol) in pyridine (4 mL) were heated for 3.5 hours with stirring, and the reaction solvent was removed under reduced pressure. To the resulting residue was added water and chloroform for extraction, and the organic layer was dried over anhydrous magnesium sulfate. The solvent was evaporated under reduced pressures, and the residue obtained was purified by silica gel column chromatography (chloroform/methanol). The resulting Adduct 42c (0.36 g, 0.92 mmol) was dissolved in chloroform (4 mL). To the solution were added methanesulfonyl chloride (0.142 mL, 1.84 mmol) and pyridine (0.074 mL, 0.92 mmol), the mixture was stirred at room temperature for 20 hours and at 50° C. for 7 hours with heating, and then the solvent was evaporated under reduced pressure. To the residue was added water, and the mixture was extracted with chloroform. The organic layer was dried over anhydrous magnesium sulfate and then concentrated. The residue obtained was purified by silica gel column chromatography (chloroform/methanol) and crystallized (hexane/ether) to obtain Compound 42 (0.11 g, 26%).

Melting point: 123–124° C.

Optical rotation: $[\alpha]_D^{24}$ −206.4° {c 1.02, CHCl$_3$, >99.5% ee [CHIRALCEL OD column (4.6×250 mm), Daicel Chemical Industries, elution solvent: ethanol]}

$^1$H NMR (270 MHz, CDCl$_3$) δ: 0.97 (t, 3H, J=7.4 Hz), 1.75–1.83 (m, 2H), 3.02 (dd, 1H, J=13.9, 7.8 Hz), 3.23 (dd, 1H, J=13.9, 4.6 Hz), 4.06–4.12 (m, 3H), 4.22 (dd, 1H, J=11.9, 9.9 Hz), 4.72–4.73 (m, 1H), 7.10 (dd, 1H, J=1.8, 0.7 Hz), 7.28–7.36 (m, 5H), 7.52 (d, 1H, J=1.8 Hz), 8.31 (d, 1H, J=0.7 Hz)

IR (KBr): 1713, 1709, 1687, 1166, 748 cm$^{-1}$

EI-MS: m/e 375 (M$^+$)

Elemental analysis: for $C_{21}H_{21}N_5O_2 \cdot HCl$

Calculated (%): C, 61.24; H, 5.38; N, 17.00 Found (%): C, 61.54; H, 5.28; N, 17.22

Example 41

Compound 43

By using 8-tert-butyl-3-propyl-6-thioxanthine, which was obtained from Compound 42a and pivaloyl chloride in the same manner as Example 40, the 6-methylthio derivative (Compound 43a) was obtained in the same manner as Example 40. Compound 43 was obtained from Compound 43a and (R)-phenylalaninol in the same manner as Example 1.

Yield: 40%

Melting point: 220–222° C. (diethyl ether/ethanol)

Optical rotation: $[\alpha]_D^{25}$ -26.80° (c 1.00, $CHCl_3$)

$^1$H-NMR (270 MHz, DMSO-$d_6$) δ: 0.86 (t, 3H, J=7.5 Hz), 1.36 (s, 9H), 1.68 (m, 2H), 3.02 (dd, 1H, J=13.9, 5.9 Hz), 3.07 (dd, 1H, J=13.9, 6.3 Hz), 3.94 (m, 1H), 3.94 (t, 2H, J=6.9 Hz), 4.20 (t, 1H, J=11.2 Hz), 4.72 (m, 1H), 7.24–7.32 (m, 5H), 10.3 (brs, 1H), 13.9 (brs, 1H)

IR ($CHCl_3$): 1714, 1699, 1687, 1673, 1587 cm$^{-1}$

FAB-MS: m/e 366 (M$^+$+1)

Elemental analysis; for $C_{21}H_{27}N_5O \cdot HCl$

Calculated (%): C, 62.75; H, 7.02; N, 17.42 Found (%): C, 62.64; H, 7.27; N, 17.47

Example 42

Compound 44

By using 3-propyl-8-(3-thienyl)-6-thioxanthine obtained in the same manner as Example 40, the 6-methylthio derivative (Compound 44a) was obtained in the same manner as Example 40.

Compound 44 was obtained from Compound 44a and (R)-phenylalaninol in the same manner as Example 1.

Yield: 39%

Melting point: 196–197° C. (ethanol)

Optical rotation: $[\alpha]_D^{24}$ -112.04° {c 0.40, $CHCl_3$, >99.5% ee [CHIRALCEL OD column (4.6×250 mm), Daicel Chemical Industries, elution solvent: ethanol]}

$^1$H NMR (270 MHz, $CDCl_3$) δ: 0.98 (t, 3H, J=7.4 Hz), 1.82 (quin, 2H, J=7.6 Hz), 3.04 (dd, 1H, J=13.9, 7.4 Hz), 3.23 (dd, 1H, J=13.9, 4.6 Hz), 4.08–4.15 (m, 3H), 4.26 (dd, 1H, J=11.9, 9.6 Hz), 4.69–4.79 (m, 1H), 7.25–7.38 (m, 5H), 7.45 (dd, 1H, J=5.3, 2.8 Hz), 7.74 (dd, 1H, J=5.3, 1.0 Hz), 8.2 (dd, 1H, J=2.8, 1.0 Hz), 11.1 (brs, 1H), 14.4 (brs, 1H).

IR (KBr): 1712, 1687, 1587 cm$^{-1}$

EI-MS: m/e 427 (M$^+$)

Elemental analysis: for $C_{21}H_{21}N_5OS \cdot HCl \cdot 0.2H_2O$

Calculated (%): C, 58.45; H, 5.23; N, 16.23 Found (%): C, 58.44; H, 5.44; N, 15.87

Example 43

Compound 45

Compound 45 was obtained from Compound 38a and 4-bromophenylalaninol in the same manner as Example 1.

Yield: 51%

Melting point: 210–212° C. (ethanol)

$^1$H-NMR (270 MHz, DMSO-$d_6$) δ: 0.86 (t, 3H, J=7.3 Hz), 1.22–1.80 (m, 10H), 1.97–2.24 (m, 2H), 2.89 (m, 1H), 3.02 (m, 2H), 3.89–3.97 (m, 3H), 4.20 (t, 1H, J=10.9 Hz), 4.70 (m, 1H), 7.29 (d, 2H, J=7.9 Hz), 7.51 (d, 2H, J=7.9 Hz)

IR (neat): 172, 1716, 1677, 1674, 1587 cm$^{-1}$

EI-MS: m/e 469 (M$^+$)

Elemental analysis: for $C_{23}H_{28}BrN_5O \cdot HCl$

Calculated (%): C, 54.50; H, 5.77; N, 13.82 Found (%): C, 54.56; H, 6.00; N, 13.60

Example 44

Compound 46

Compound 46 was obtained from Compound 35a and 4-chlorophenylalaninol in the same manner as Example 1.

Yield: 63%

Melting point: 191–192° C. (ethanol/diisopropyl ether)

$^1$H NMR (270 MHz, $CDCl_3$) δ: 0.96 (t, 3H, J=7.3 Hz), 1.03 (t, 3H, J=7.3 Hz), 1.70–1.80 (m, 2H), 1.81–1.94 (m, 2H), 2.85 (t, 2H, J=7.8 Hz), 3.03 (dd, 1H, J=14.2, 6.9 Hz), 3.16 (dd, 1H, J=14.2, 4.6 Hz), 4.01–4.09 (m, 3H), 4.26 (dd, 1H, J=11.9, 9.9 Hz), 4.67–4.69 (m, 1H), 7.23 (d, 2H, J=8.6 Hz), 7.31 (d, 2H, J=8.6 Hz), 11.5 (brs, 1H), 13.6 (brs, 1H)

IR (KBr): 1716, 1679, 1591 cm$^{-1}$

EI-MS: m/e 385 (M$^+$)

Elemental analysis: for $C_{20}H_{24}ClN_5O \cdot HCl$

Calculated (%): C, 56.90; H, 5.69; N, 16.60 Found (%): C, 56.66; H, 6.07; N, 16.50

Example 45

Compound 47

Compound 47 was obtained from Compound 38a and 4-chlorophenylalaninol in the same manner as Example 1.

Yield: 64%

Melting point: 235–236° C. (methanol/diisopropyl ether)

$^1$H NMR (270 MHz, $CDCl_3$) δ: 0.95 (t, 3H, J=7.4 Hz), 1.28–1.89 (m, 8H), 2.10–2.17 (m, 2H), 2.81–2.91 (m, 1H), 3.02 (dd, 1H, J=14.0, 7.1 Hz), 3.16 (dd, 1H, J=14.0, 4.8 Hz), 4.00–4.09 (m, 3H), 4.24 (dd, 1H, J=11.9, 9.9 Hz), 4.65–4.67 (m, 1H), 7.2 (d, 2H, J=8.3 Hz), 7.22 (d, 2H, J=8.3 Hz), 7.31 (d, 2H, J=8.3 Hz), 11.5 (brs, 1H), 13.6 (brs, 1H)

IR (KBr): 1716, 1675, 1587 cm$^{-1}$

EI-MS: m/e 425 (M$^+$)

Elemental analysis: for $C_{23}H_{28}ClN_5O \cdot HCl$

Calculated (%): C, 59.74; H, 6.32; N, 15.14 Found (%): C, 60.03; H, 6.38; N, 15.38

Example 46

Compound 48

Compound 48 was obtained from Compound 37a and 4-chlorophenylalaninol in the same manner as Example 1.

Yield: 64%

Melting point: 214–215° C. (dioxane/diisopropyl ether)

$^1$H NMR (270 MHz, $CDCl_3$) δ: 0.96 (t, 3H, J=7.4 Hz), 1.71–1.84 (m, 2H), 2.01–2.17 (m, 2H), 2.39–2.49 (m, 4H), 3.02 (dd, 1H, J=14.0, 7.1 Hz), 3.16 (dd, 1H, J=14.0, 4.8 Hz), 3.65–3.78 (m, 1H), 4.00–4.10 (m, 3H), 4.25 (dd, 1H, J=11.9, 9.9 Hz), 4.64–4.72 (m, 1H), 7.22 (d, 2H, J=8.6 Hz), 7.32 (d, 2H, J=8.6 Hz), 11.5 (brs, 1H), 13.6 (brs, 1H)

IR (KBr): 1716, 1679, 1587 cm$^{-1}$

EI-MS: m/e 397 (M$^+$)

Elemental analysis: for $C_{21}H_{24}ClN_5O \cdot HCl$

Example 47

Compound 49

Compound 49 was obtained from Compound 35a and 4-fluorophenylalaninol in the same manner as Example 1.

Yield: 59%

Melting point: 199–200° C. (ethanol/diisopropyl ether)

$^1$H NMR (270 MHz, CDCl$_3$) δ: 0.95 (t, 3H, J=7.4 Hz), 1.03 (t, 3H, J=7.4 Hz), 1.72–1.94 (m, 4H), 2.85 (t, 2H, J=7.8 Hz), 2.99–3.18 (m, 2H), 4.03–4.09 (m, 3H), 4.24 (t, 1H, J=10.7 Hz), 4.60–4.80 (m, 1H), 7.02 (t, 2H, J=8.4 Hz), 7.24–7.28 (m, 2H), 11.5 (brs, 1H)

IR (KBr): 1714, 1575, 1510 cm$^{-1}$

EI-MS: m/e 369 (M$^+$)

Elemental analysis: for C$_{20}$H$_{24}$FN$_5$O.HCl

Calculated (%): C, 59.18; H, 6.21; N, 17.25 Found (%): C, 59.14; H, 6.44; N, 17.15

Example 48

Compound 50

Compound 50 was obtained from Compound 38a and 4-fluorophenylalaninol in the same manner as Example 1.

Yield: 46%

Melting point: 237–239° C. (ethanol/diisopropyl ether)

$^1$H NMR (270 MHz, CDCl$_3$) δ: 0.95 (t, 3H, J=7.4 Hz), 1.26–1.89 (m, 10H), 2.11–2.15 (m, 2H), 2.86 (tt, 1H, J=11.6, 3.5 Hz), 3.02 (dd, 1H, J=14.0, 6.9 Hz), 3.17 (dd, 1H, J=14.0, 4.6 Hz), 4.02–4.09 (m, 3H), 4.24 (dd, 1H, J=11.9, 9.9 Hz), 4.63–4.73 (m, 1H), 7.02 (t, 2H, J=8.6 Hz), 7.23–7.28 (m, 2H), 11.4 (brs, 1H), 13.6 (brs, 1H)

IR (KBr): 1718, 1714, 1589, 1510 cm$^{-1}$

EI-MS: m/e 407 (M$^+$)

Elemental analysis: for C$_{23}$H$_{28}$FN$_5$O.HCl

Calculated (%): C, 61.94; H, 6.55; N, 15.70 Found (%): C, 62.05; H, 6.83; N, 15.74

Example 49

Compound 51

According to a known method, (R)-4-fluorophenylalaninol was obtained from (R)-4-fluorophenylalanine hydrochloride.

Compound 51 was obtained from Compound 37a and (R)-4-fluorophenylalaninol in the same manner as Example 1.

Yield: 37%

Melting point: 240–245° C. (ethyl acetate/acetone)

Optical rotation: [α]$_D^{24}$–16.2° {c 1.03, CHCl$_3$, >99.5% ee [CHIRALCEL OD column (4.6×250 mm), Daicel Chemical Industries, elution solvent: ethanol]}

$^1$H NMR (270 MHz, CDCl$_3$) δ: 0.96 (t, 3H, J=7.6 Hz), 1.78 (quin, 2H, J=7.2 Hz), 2.04–2.14 (m, 2H), 2.40–2.50 (m, 4H), 3.02 (dd, 1H, J=13.8, 6.9 Hz), 3.17 (dd, 1H, J=12.7, 4.9 Hz), 3.72 (quin, 1H, J=8.5 Hz), 4.05 (t, 2H, J=5.9 Hz), 4.08 (dd, 1H, J=7.6, 2.6 Hz), 4.25 (dd, 1H, J=9.9, 2.3 Hz), 4.68 (m, 1H), 7.04 (t, 2H, J=8.5 Hz), 7.24–7.29 (m, 2H), 11.41 (brs, 1H), 13.70 (brs, 1H)

IR (KBr): 1721, 1712, 1610, 1518 cm$^{-1}$

EI-MS: m/e 381 (M$^+$)

Elemental analysis: for C$_{21}$H$_{24}$FN$_5$O.HCl

Calculated (%): C, 60.35; H, 6.03; N, 16.76 Found (%): C, 60.57; H, 6.22; N, 16.71

Example 50

Compound 52

By using 8-butyl-3-propyl-6-thioxanthine obtained in the same manner as Example 40, the 6-methylthio derivative (Compound 52a) was obtained in the same manner as Example 40.

Compound 52 was obtained from Compound 52a and 4-fluorophenylalaninol in the same manner as Example 1.

Yield: 20%

Melting point: 193–196° C. (acetone/ether)

$^1$H NMR (270 MHz, CDCl$_3$) δ: 0.95 (t, 3H, J=7.2 Hz), 0.97 (t, 3H, J=7.2 Hz), 1.43 (q, 2H, J=7.6 Hz), 1.78 (quin, 4H, J=7.6 Hz), 2.87 (t, 2H, J=7.6 Hz), 3.02 (dd, 1H, J=14.1, 6.9 Hz), 3.16 (dd, 1H, J=14.1, 4.9 Hz), 4.05 (dd, 1H, J=12.2, 6.6 Hz), 4.06 (t, 2H, J=7.2 Hz), 4.24 (dd, 1H, J=11.9, 9.6 Hz), 4.66 (m, 1H), 7.03 (t, 2H, J=8.6 Hz), 7.23–7.28 (m, 2H), 11.47 (brs, 1H), 13.63 (brs, 1H)

IR (KBr): 172, 1699, 1678, 1653, 1591 cm$^{-1}$

EI-MS: m/e 383 (M$^+$)

Elemental analysis: for C$_{21}$H$_{26}$FN$_5$O.HCl

Calculated (%): C, 60.07; H, 6.48; N, 16.67 Found (%): C, 59.98; H, 6.62; N, 16.75

Example 51

Compound 53

Compound 53 was obtained from 8-(2-furyl)-6-methylthio-3-propyl-7H-purin-2(3H)-one (Compound 53a), which was obtained in the same manner as Example 40, and 4-fluorophenylalaninol in the same manner as Example 1.

Yield: 36%

Melting point: 194–195° C. (diethyl ether/hexane)

$^1$H NMR (270 MHz, CDCl$_3$) δ: 0.97 (t, 3H, J=7.4 Hz), 1.66–1.87 (quin, 2H, J=7.5 Hz), 3.05 (dd, 1H, J=13.9, 7.1 Hz), 3.18 (dd, 1H, J=13.9, 4.5 Hz), 4.04–4.14 (m, 3H), 4.26 (dd, 1H, J=11.9, 9.9 Hz), 4.68–4.78 (m, 1H), 6.61 (dd, 1H, J=3.6, 2.0 Hz), 7.38 (d, 1H, J=3.6 Hz), 7.03 (t, 2H, J=8.6 Hz), 7.68 (d, 1H, J=2.0 Hz), 7.26 (t, 2H, J=8.6 Hz), 11.7 (brs, 1H), 14.3 (brs, 1H)

IR (KBr): 1716, 1706, 1700, 1683, 1585 cm$^{-1}$

EI-MS: m/e 393 (M$^+$)

Elemental analysis: for C$_{21}$H$_{20}$FN$_5$O$_2$.HCl.0.8H$_2$O

Calculated (%): C, 56.77; H, 5.13; N, 15.76 Found (%): C, 56.78; H, 5.08; N, 15.33

Example 52

Compound 54

Compound 54 was obtained from Compound 42b and (R)-4-fluorophenyl-alaninol in the same manner as Example 1.

Yield: 35%

Melting point: 149–150° C. (diethyl ether/hexane)

Optical rotation: [α]$_D^{24}$–349.1° {c 1.03, CHCl$_3$, >99.5% ee [CHIRALCEL OD column (4.6×250 mm), Daicel Chemical Industries, elution solvent: ethanol]} $^1$H NMR (270 MHz, CDCl$_3$) δ: 1.03 (t, 3H, J=7.4 Hz), 1.85–1.93 (m, 2H), 2.65 (d, 2H, J=6.6 Hz), 3.87–3.90 (m, 1H), 4.10–4.18 (m, 4H), 6.78 (s, 2H), 6.80 (s, 2H), 6.86 (d, 1H, J=1.3 Hz), 7.46–7.47 (m, 1H), 8.03 (s, 1H)

IR (KBr): 1695, 1685, 1510, 752 cm$^{-1}$

EI-MS: m/e 393 (M$^+$)

Elemental analysis: for C$_{21}$H$_{20}$FN$_5$O$_2$

Calculated (%): C, 64.11; H, 5.12; N, 17.80 Found (%): C, 64.04; H, 5.30; N, 17.78

Example 53

Compound 55

Compound 55 was obtained from Compound 43a and (R)-4-fluorophenyl-alaninol in the same manner as Example 1.

Yield: 60%

Melting point: 232–236° C. (diethyl ether/ethanol)

Optical rotation: [α]$_D^{25}$ –14.3° {c 1.00, CHCl$_3$>99.5% ee [CHIRALCEL OD column (4.6×250 mm), Daicel Chemical Industries, elution solvent: ethanol]}

$^1$H-NMR (270 MHz, DMSO-d$_6$) δ: 0.86 (t, 3H, J=7.3 Hz), 1.36 (s, 9H), 1.68 (m, 2H), 3.04 (m, 2H), 3.95 (m, 1H), 3.95 (t, 2H, J=5.7 Hz), 4.21 (t, 1H, J=10.5 Hz), 4.69 (m, 1H), 7.13 (dd, 2H, J=8.9, 8.4 Hz), 7.36 (dd, 2H, J=8.4, 5.4 Hz), 10.4 (brs, 1H), 13.9 (brs, 1H)

IR (neat): 1714, 1679, 1583, 1510 cm$^{-1}$

EI-MS: m/e 384 (M$^+$+1)

Elemental analysis: for C$_{21}$H$_{26}$FN$_5$O.HCl

Calculated (%): C, 60.06; H, 6.48; N, 16.68 Found (%): C, 60.16; H, 6.81; N, 16.80

Example 54

Compound 56

Compound 56 was obtained from Compound 35a and 3-fluorophenylalaninol in the same manner as Example 1.

Yield: 49%

Melting point: 139–140° C. (ethanol/diisopropyl ether)

$^1$H NMR (270 MHz, CDCl$_3$) δ: 0.96 (t, 3H, J=7.4 Hz), 1.03 (t, 3H, J=7.3 Hz), 1.73–1.94 (m, 4H), 2.85 (t, 2H, J=7.6 Hz), 3.00–3.05 (m, 1H), 3.22–3.27 (m, 1H), 4.04–4.10 (m, 3H), 4.20–4.35 (m, 1H), 4.60–4.83 (m, 1H), 6.96–7.01 (m, 2H), 7.06–7.09 (m, 1H), 7.31–7.36 (m, 1H), 11.5 (brs, 1H)

IR (KBr): 1712, 1672, 1585, 1390 cm$^{-1}$

EI-MS: m/e 369 (M$^+$)

Elemental analysis: for C$_{20}$H$_{24}$FN$_5$O.HCl.H$_2$O

Calculated (%): C, 56.67; H, 6.42; N, 16.52 Found (%): C, 56.82; H, 6.67; N, 16.48

Example 55

Compound 57

Compound 57 was obtained from Compound 37a and 3-fluorophenylalaninol in the same manner as Example 1.

Yield: 52%

Melting point: 164–165° C. (ethanol/diisopropyl ether)

$^1$H NMR (270 MHz, CDCl$_3$) δ: 0.97 (t, 3H, J=7.4 Hz), 1.72–1.85 (m, 2H), 1.99–2.17 (m, 2H), 2.40–2.49 (m, 4H), 3.01 (dd, 1H, J=13.9, 7.6 Hz), 3.24 (dd, 1H, J=13.9, 4.6 Hz), 3.65–3.78 (m, 1H), 4.02–4.11 (m, 3H), 4.25 (t, 1H, J=10.7 Hz), 4.60–4.75 (m, 1H), 6.96–7.08 (m, 3H), 7.29–7.37 (m, 1H), 11.5 (brs, 1H), 13.7 (brs, 1H)

IR (KBr): 1722, 1685, 1591, 1515 cm$^{-1}$

EI-MS: m/e 381 (M$^+$)

Elemental analysis: for C$_{21}$H$_{24}$FN$_5$O.HCl

Calculated (%): C, 60.35; H, 6.03; N, 16.76 Found (%): C, 60.57; H, 6.22; N, 16.71

Example 56

Compound 58

Compound 58 was obtained from 8-isobutyl-6-methylthio-3-propyl-7H-purin-2(3H)-one (Compound 58a), which was obtained in the same manner as Example 40, and 3-fluorophenylalaninol in the same manner as Example 1.

Yield: 86%

Melting point: 186–187° C. (chloroform/diisopropyl ether)

$^1$H NMR (270 MHz, CDCl$_3$) δ: 0.89–0.95 (m, 6H), 1.01 (t, 3H, J=7.3 Hz), 1.84 (m, 2H), 2.06 (m, 1H), 2.44 (dd, 1H, J=14.2, 7.6 Hz), 2.62 (dd, 1H, J=14.2, 7.3 Hz), 2.74–2.87 (m, 2H), 3.73 (m, 1H), 3.94–4.08 (m, 4H), 6.75–6.92 (m, 3H), 7.08 (m, 1H)

IR (KBr): 1701, 1653, 1543, 1491 cm$^{-1}$

FAB-MS: m/e 384 (M$^+$+1)

Elemental analysis: for C$_{21}$H$_{26}$FN$_5$O

Calculated (%): C, 65.78; H, 6.83; N, 18.26 Found (%): C, 65.80; H, 7.11; N, 18.54

Example 57

Compound 59

Compound 59 was obtained from 8-(4-bromophenyl)-6-methylthio-3-propyl-7H-purin-2(3H)-one (Compound 59a), which was obtained in the same manner as Example 40, and 3-fluorophenylalaninol in the same manner as Example 1.

Yield: 21%

Melting point: 224–226° C. (ethyl acetate)

$^1$H NMR (270 MHz, CDCl$_3$) δ: 0.99 (t, 3H, J=7.4 Hz), 1.81 (m, 2H), 3.05 (q, 1H, J=7.3 Hz), 3.21 (dd, 1H, J=11.7, 4.5 Hz), 4.07–4.15 (m, 3H), 4.31 (dd, 1H, J=12.2, 10.0 Hz), 4.75 (m, 1H), 6.97–7.02 (m, 2H), 7.08 (d, 1H, J=7.6 Hz), 7.34 (m, 1H), 7.65 (d, 2H, J=8.5 Hz), 8.01 (d, 2H, J=8.5 Hz)

IR (KBr): 1706, 1585, 1412, 1351, 1268, 1143, 1070, 1010, 845, 746, 692 cm$^{-1}$

EI-MS: m/e 481 (M$^+$)

Elemental analysis: for C$_{23}$H$_{21}$BrFN$_5$O.HCl.0.25CH$_3$CO$_2$C$_2$H$_5$ Calculated (%): C, 53.30; H, 4.47; N, 12.95 Found (%): C, 53.69; H, 4.41; N, 13.01

Example 58

Compound 60

Compound 60 was obtained from Compound 58a and 2-fluorophenylalaninol (Indian Journal of Chemistry, Section B, vol. 15B, p.260, 1977) in the same manner as Example 1.

Yield: 87%

Melting point: 159–160° C. (chloroform/diisopropyl ether)

$^1$H NMR (270 MHz, CDCl$_3$) δ: 0.90–1.03 (m, 9H), 1.82 (m, 2H), 2.12 (m, 1H), 2.51 (dd, 1H, J=14.2, 7.3 Hz), 2.67 (dd, 1H, J=14.2, 7.3 Hz), 2.78–2.95 (m, 2H), 3.75 (dd, 1H,

J=11.2, 5.9 Hz), 3.94–4.16 (m, 4H), 6.82 (m, 1H), 6.92 (m, 1H), 7.06–7.11 (m, 2H)

IR (KBr): 1701, 1649, 1545, 1500, 1265 cm$^{-1}$

FAB-MS: m/e 384 (M$_+$+1)

Elemental analysis: for $C_{21}H_{26}FN_5O$

Calculated (%): C, 65.78; H, 6.83; N, 18.26 Found (%): C, 65.83; H, 7.00; N, 18.42

The aminoalcohols used in Examples 59 to 65 were obtained by a known method [Chemical and Pharmaceutical Bulletin, vol. 13 (8), p.995, 1965] from substituted phenylalanine methyl ester hydrochlorides obtained by a known method.

Example 59

Compound 61

Compound 61 was obtained from Compound 6a and 3-methylphenylalaninol in the same manner as Example 1.

Yield: 50%

Melting point: 157–159° C. (ethyl acetate/diisopropyl ether)

$^1$H NMR (270 MHz, CDCl$_3$) δ: 0.97 (t, 3H, J=7.4 Hz), 1.67–2.09 (m, 10H), 2.23 (m, 3H), 2.82 (dd, 1H, J=13.5, 6.9 Hz), 2.97 (dd, 1H, J=13.5, 6.6 Hz), 3.15–3.21 (m, 1H), 3.85 (dd, 1H, J=6.6 Hz), 4.02–4.09 (m, 3H), 4.25–4.31 (m, 1H), 6.89 (brs, 1H), 6.96–7.26 (m, 4H)

IR (KBr): 1702, 1681, 1542 cm$^{-1}$

EI-MS: m/e 391 (M$^+$)

Elemental analysis: for $C_{23}H_{29}N_5O \cdot 0.5H_2O$

Calculated (%): C, 68.97; H, 7.55; N, 17.49 Found (%): C, 69.30; H, 7.70; N, 17.42

Example 60

Compound 62

Compound 62 was obtained from Compound 6a and 3-iodophenylalaninol in the same manner as Example 1.

Yield: 35%

Melting point: 146–148° C. (acetone/ether)

$^1$H NMR (270 MHz, CDCl$_3$) δ: 0.96 (t, 3H, J=7.4 Hz), 1.70–1.89 (m, 8H), 2.13–2.23 (m, 2H), 2.95 (dd, 1H, J=13.0, 7.3 Hz), 3.15 (dd, 1H, J=13.0, 4.8 Hz), 3.28 (quin, 1H, J=7.9 Hz), 4.04 (dd, 1H, J=8.8, 2.9 Hz), 4.07 (t, 2H, J=6.6 Hz), 4.23 (t, 1H, J=9.7 Hz), 4.68 (m, 1H), 7.08 (t, 1H, J=7.9 Hz), 7.24 (d, 1H, J=1.0 Hz), 7.61 (dd, 2H, J=7.9, 1.0 Hz)

IR (KBr): 1714, 1684, 1670, 1587 cm$^{-1}$

EI-MS: m/e 503 (M$^+$)

Elemental analysis: for $C_{22}H_{26}N_5OI \cdot HCl$

Calculated (%): C, 48.95; H, 5.04; N, 12.97 Found (%): C, 48.87; H, 5.14; N, 12.75

Example 61

Compound 63

Compound 63 was obtained from Compound 6a and 2,3-difluorophenylalaninol in the same manner as Example 1.

Yield: 53%

Melting point: 185–187° C. (diisopropyl ether/ethanol)

$^1$H-NMR (270 MHz, DMSO-d$_6$) δ: 0.90 (t, 3H, J=7.6 Hz), 1.65–1.77 (m, 8H), 2.08 (m, 2H), 3.17 (m, 2H), 3.29 (m, 1H), 3.96 (t, 2H, J=11.2 Hz), 3.96 (m, 1H), 4.30 (t, 1H, J=10.6 Hz), 4.73 (m, 1H), 7.16–7.41 (m, 3H), 10.6 (brs, 1H), 13.8 (brs, 1H)

IR (neat): 1714, 1682, 1587, 1489 cm$^{-1}$

FAB-MS: m/e 414 (M$^+$+1)

Elemental analysis: for $C_{22}H_{25}F_2N_5O \cdot HCl \cdot 0.3H_2O$

Calculated (%): C, 58.03; H, 5.89; N, 15.38 Found (%): C, 57.92; H, 5.88; N, 15.60

Example 62

Compound 64

Compound 64 was obtained from Compound 6a and 2,5-difluorophenylalaninol in the same manner as Example 1.

Yield: 35%

Melting point: 198–202° C. (acetone/ether)

$^1$H NMR (270 MHz, CDCl$_3$) δ: 0.97 (t, 3H, J=7.5 Hz), 1.67–1.92 (m, 8H), 2.04–2.23 (m, 2H), 3.04 (dd, 1H, J=13.6, 7.2 Hz), 3.21–3.36 (m, 2H), 3.98–4.14 (m, 3H), 4.27 (dd, 1H, J=12.2, 9.6 Hz), 4.73 (m, 1H), 6.93–7.18 (m, 3H), 11.56 (brs, 1H), 13.44 (brs, 1H)

IR (KBr): 1716, 1684, 1652, 1585, 1506, 1498 cm$^{-1}$

EI-MS: m/e 413 (M$^+$)

Elemental analysis: for $C_2H_{25}F_2N_5O \cdot HCl \cdot 0.1H_2O$

Calculated (%): C, 58.50; H, 5.85; N, 15.50 Found (%): C, 58.57; H, 5.86; N, 15.43

Example 63

Compound 65

Compound 65 was obtained from Compound 6a and 2,5-dichlorophenylalaninol in the same manner as Example 1.

Yield: 42%

Melting point: 172–173° C. (ethyl acetate/ether)

$^1$H NMR (270 MHz, CDCl$_3$) δ: 0.98 (t, 3H, J=7.4 Hz), 1.67–1.94 (m, 8H), 2.12–2.22 (m, 2H), 3.12 (dd, 1H, J=14.2, 7.8 Hz), 3.25–3.31 (m, 1H), 3.37 (dd, 1H, J=14.2, 5.6 Hz), 4.05–4.13 (m, 3H), 4.26 (dd, 1H, J=11.9, 9.9 Hz), 4.76–4.82 (m, 1H), 7.22–7.28 (m, 1H), 7.34–7.38 (m, 2H), 11.5 (brs, 1H)

IR (KBr): 1714, 1668, 1585 cm$^{-1}$

EI-MS: m/e 445 (M$^+$)

Elemental analysis: for $C_{22}H_{25}Cl_2N_5O \cdot HCl$

Calculated (%): C, 54.72; H, 5.18; N, 14.50 Found (%): C, 55.03; H, 5.27; N, 14.61

Example 64

Compound 66

Compound 66 was obtained from Compound 3a and (S)-tert-leucinol in the same manner as Example 1.

Yield: 27%

Melting point: 230–233° C. (acetone/ether)

Optical purity; >99% ee [CHIRALCEL OD column (4.6× 250 mm), Daicel Chemical Industries, elution solvent: ethanol]

$^1$H NMR (270 MHz, CDCl$_3$) δ: 0.98 (t, 3H, J=7.6 Hz), 1.06 (s, 9H), 1.62–1.73 (m, 3H), 1.82 (q, 2H, J=7.3 Hz), 1.94–2.02 (m, 3H), 2.03 (d, 2H, J=10.9 Hz), 2.24 (d, 2H, J=10.4 Hz), 2.41 (brs, 2H), 2.70 (t, 1H, J=6.6 Hz), 4.12 (t, 2H, J=7.3 Hz), 4.14–4.26 (m, 3H), 11.29 (brs, 1H), 13.54 (brs, 1H)

IR (CHCl$_3$) 1816, 1794, 1714, 1683, 1652, 1585 cm$^{-1}$

EI-MS: m/e 395 (M$^+$)

Elemental analysis: for $C_{23}H_{33}N_5O\cdot HCl\cdot 0.2H_2O$

Calculated (%): C, 63.42; H, 7.96; N, 16.08 Found (%): C, 63.52; H, 8.16; N, 15.94

Example 65

Compound 67

Compound 67 was obtained from Compound 42b and (S)-tert-leucinol in the same manner as Example 40.

Yield: 38%

Melting point: 204–206° C. (ethyl acetate/hexane)

Optical rotation: $[\alpha]_D^{24}$253.9° {c 1.03, CHCl$_3$, >99% ee [CHIRALCEL OD column (4.6×250 mm), Daicel Chemical Industries, elution solvent: ethanol]}

$^1$H NMR (270 MHz, CDCl$_3$) δ: 0.77 (s, 9H), 1.01 (t, 3H, J=7.6 Hz), 1.86 (quin, 2H, J=7.3 Hz), 3.87 (dd, 1H, J=10.5, 6.3 Hz), 4.03 (dd, 1H, J=12.2, 6.1 Hz), 4.16 (m, 3H), 6.89 (s, 1H), 7.45 (s, 1H), 8.06 (s, 1H)

IR (KBr): 1689, 1683, 1548, 1514, 1371, 1306 cm$^{-1}$

EI-MS: m/e 341 (M$^+$)

Elemental analysis: for $C_{18}H_{23}N_5O_2\cdot H_2O$

Calculated (%): C, 60.15; H, 7.01; N, 19.48 Found (%): C, 60.24; H, 7.28; N, 19.49

Example 66

Compound 68

Compound 68 was obtained from 8-(3,5-dimethylisoxazol-4-yl)-6-methylthio-3-propyl-7H-purin-2(3H)-one (Compound 68a), which was obtained in the same manner as Example 40, and (S)-tert-leucinol in the same manner as Example 1.

Yield: 63%

Melting point: 185–186° C. (ethyl acetate/hexane)

Optical rotation: $[\alpha]_D^{25}$–13.68° {c 1.01, CHCl$_3$, >99.5% ee [CHIRALCEL OD column (4.6×250 mm), Daicel Chemical Industries, elution solvent: ethanol]}

$^1$H NMR (270 MHz, CDCl$_3$) δ: 1.01 (t, 3H, J=7.4 Hz), 1.09 (s, 9H), 1.79–1.93 (m, 2H), 2.67 (s, 3H), 2.87 (s, 3H), 4.09–4.32 (m, 5H), 11.8 (brs, 1H), 13.9 (brs, 1H)

IR (KBr): 1714, 1685, 1413 cm$^{-1}$

FAB-MS: m/e 371 (M$^+$+1)

Example 67

Compound 69

Compound 69 was obtained from Compound 41a and (S)-valinol in the same manner as Example 1.

Yield: 55%

Melting point: 156–157° C. (dioxane/ether)

Optical rotation: $[\alpha]_D^{25}$–44.14° {c 1.01, CHCl$_3$, >99.5% ee [CHIRALCEL OD column (4.6×250 mm), Daicel Chemical Industries, elution solvent: ethanol]}

$^1$H NMR (270 MHz, CDCl$_3$) δ: 0.99 (t, 3H, J=7.4 Hz), 1.06 (d, 3H, J=6.9 Hz), 1.15 (d, 3H, J=6.6 Hz), 1.42 (d, 6H, J=6.9 Hz), 1.64–1.86 (m, 2H), 1.93–2.01 (m, 1H), 3.17 (quin, 1H, J=6.9 Hz), 4.01 (dd, 1H, J=11.1, 7.1 Hz), 4.08–4.22 (m, 3H), 4.33 (dd, 1H, J=11.1, 10.1 Hz), 11.5 (brs, 1H), 13.6 (brs, 1H)

IR (KBr): 1712, 1687, 1592 cm$^{-1}$

EI-MS: m/e 304 (M$^+$)

Elemental analysis: for $C_{16}H_{25}N_5O\cdot HCl$

Calculated (%): C, 56.54; H, 7.71; N, 20.61 Found (%): C, 56.69; H, 7.95; N, 20.61

Example 68

Compound 70

3-Cyanophenylalanine methyl ester hydrochloride disclosed in DE19544687 was converted into an amino alcohol by a known method [Chemical and Pharmaceutical Bulletin, vol. 13 (8), p.995, 1965]. By using this compound and Compound 6a, Compound 70 was obtained in the same manner as Example 1.

Yield: 58%

$^1$H-NMR (270 MHz, CDCl$_3$) δ: 0.99 (t, 3H, J=7.3 Hz), 1.63–1.94 (m, 10H), 2.80 (m, 1H), 2.95 (dd, 1H, J=13.5, 5.3 Hz), 3.04 (dd, 1H, J=13.5, 8.9 Hz), 3.80 (dd, 1H, J=11.2, 6.3 Hz), 4.00 (t, 2H, J=7.3 Hz), 4.10 (t, 1H, J=11.2 Hz), 4.37 (m, 1H), 7.30–7.34 (m, 2H), 7.47 (d, 1H, J=6.9 Hz), 7.57 (s, 1H)

Example 69

Compound 71

Compound 71 was obtained from 8-cyclopentyl-3-ethyl-6-methylthio-7H-purin-2(3H)-one (Compound 71a), which was obtained in the same manner as Example 40, and (R)-phenylalaninol in the same manner as Example 1.

Yield: 44%

Melting point: 168–169° C. (dioxane/ether)

Optical rotation: $[\alpha]_D^{25}$–30.40° {c 1.02, CHCl$_3$, >99.5% ee [CHIRALCEL OD column (4.6×250 mm), Daicel Chemical Industries, elution solvent: ethanol]}

$^1$H NMR (270 MHz, CDCl$_3$) δ: 1.33 (t, 3H, J=7.1 Hz), 1.70–2.23 (m, 8H), 2.99 (dd, 1H, J=14.0, 7.6 Hz), 3.23 (dd, 1H, J=14.0, 4.6 Hz), 3.21–3.31 (m, 1H), 4.08 (dd, 1H, J=12.2, 6.6 Hz), 4.13–4.25 (m, 3H), 4.65–4.80 (m, 1H), 7.25–7.37 (m, 5H), 11.4 (brs, 1H), 13.7 (brs, 1H)

IR (KBr): 1720, 1712, 1679, 1591 cm$^{-1}$

FAB-MS: m/e 364 (M$^+$+1)

Elemental analysis: for $C_{21}H_{25}N_5O\cdot HCl\cdot 0.2H_2O$

Calculated (%): C, 62.50; H, 6.59; N, 17.36 Found (%): C, 62.65; H, 6.67; N, 17.36

Example 70

Compound 72

In the same manner as Example 1, Compound 72 was obtained from (R)phenylalaninol and 8-cyclopentyl-3-cyclopropylmethyl-6-methylthio-7H-purin-2(3H)one (Compound 72a), which was obtained by a known method (Journal of Medicinal Chemistry, vol. 36, p.2508, 1993) using a known compound, 5,6-diamino-1-cyclopropylmethyl-2,4-pyrimidinedione, disclosed in EP-A-386683, and (R)-phenylalaninol.

Yield: 56%

$^1$H NMR (270 MHz, CDCl$_3$) δ: 0.44–0.56 (m, 4H), 1.23–1.37 (m, 1H), 1.70–2.19 (m, 8H), 2.96 (dd, 1H, J=13.7, 7.8 Hz), 3.16–3.31 (m, 2H), 3.97 (d, 2H, J=7.3 Hz), 3.96–4.04 (m, 1H), 4.16 (t, 1H, J=10.7 Hz), 4.50–4.68 (m, 1H), 7.23–7.45 (m, 5H), 9.60 (brs, 1H)

FAB-MS: m/e 390 (M$^+$+1)

Example 71

Compound 73

Compound 73 was obtained from 8-cyclopropylmethyl-6-methylthio-3-propyl-7H-purin-2(3H)-one (Compound 73a), which was obtained in the same manner as Example 40, and (R)-phenylalaninol in the same manner as Example 1.

Yield: 56%

Melting point: 188–190° C. (ether/ethanol)

Optical rotation: $[\alpha]_D^{25}$ −2.00 (c 1.03, $CHCl_3$)

$^1$H-NMR (270 MHz, DMSO-$d_6$) δ: 0.28 (m, 2H), 0.56 (m, 2H), 0.87 (t, 3H, J=7.3 Hz), 1.05 (m, 1H), 1.66 (m, 2H), 2.78 (d, 2H, J=6.6 Hz), 3.01 (dd, 1H, J=13.2, 6.3 Hz), 3.19 (dd, 1H, J=13.2, 6.3 Hz), 3.95 (m, 1H), 3.95 (t, 2H, J=6.9 Hz), 4.20 (t, 1H, J=10.9 Hz), 4.74 (m, 1H), 7.21–7.33 (m, 5H), 10.7 (brs, 1H), 13.7 (brs, 1H)

IR (neat): 1713, 1682, 1673, 1587 $cm^{-1}$

FAB-MS: m/e 364 ($M^+$+1)

Elemental analysis: for $C_{21}H_{25}N_5O \cdot HCl$

Calculated (%): C, 63.07; H, 6.55; N, 17.51 Found (%): C, 63.04; H, 6.85; N, 17.47

Example 72

Compound 74

To Compound 70 (100 mg, 0.25 mmol) were added a 4 mol/L aqueous solution of sodium hydroxide (2 mL) and methanol (2 mL), and the mixture was stirred at 100° C. for 6 hours. The reaction mixture was neutralized with 2 mol/L hydrochloric acid, and then the solid precipitated was collected by filtration to obtain Compound 74 (84 mg, 80%) as a white solid.

Yield: 80%

Melting point: >300° C.

$^1$H-NMR (270 MHz, DMSO-$d_6$) δ: 0.84 (t, 3H, J=7.3 Hz), 1.58–1.72 (m, 8H), 1.94 (m, 2H), 2.95 (m, 2H), 3.07 (q, 1H, J=9.5 Hz), 3.59 (dd, 1H, J=11.3, 7.0 Hz), 3.83 (t, 2H, J=6.5 Hz), 3.92 (t, 1H, J=10.5 Hz), 4.50 (m, 1H), 7.34 (t, 1H, J=8.0 Hz), 7.50 (d, 1H, J=8.0 Hz), 7.76 (d, 1H, J=8.0 Hz), 7.84 (s, 1H)

IR (neat): 1713, 1674, 1662 $cm^{-1}$

EI-MS: m/e 421 ($M^+$)

Example 73

Compound 75

β,β-Dimethylphenylalanine obtained by a known method [Acta Pharmaceutica Suecica, vol. 13, p.75, 1976] was converted into 2-amino-3-methyl-3-phenyl-1-butanol by a known method. From this compound and Compound 6a, Compound 75 was obtained in the same manner as Example 1.

Yield: 25%

Melting point: 85–90° C.

$^1$H-NMR (270 MHz, $CDCl_3$) δ: 0.94 (t, 3H, J=7.3 Hz), 1.42 (s, 3H), 1.45 (s, 3H), 1.68–1.85 (m, 8H), 2.10 (m, 2H), 3.21 (q, 1H, J=7.8 Hz), 3.81 (dd, 1H, J=6.8, 11.9 Hz), 3.88 (t, 1H, J=11.9 Hz), 4.00 (t, 2H, J=7.3 Hz), 4.41 (dd, 1H, J=6.8, 9.5 Hz), 7.16–7.38 (m, 5H)

IR (neat): 1716, 1704, 1693, 1660 $cm^{-1}$

EI-MS: m/e 405 ($M^+$)

Example 74

Compound 76

To a solution of Compound 27 (91.2 mg, 0.176 mmol) in methanol (2.0 mL) were added 20% $Pd(OH)_2$/C (15 mg) and ammonium formate (90 mg) and the mixture was refluxed for 2 hours. The reaction mixture was filtered and concentrated, to the residue was added water and the mixture was extracted with ethyl acetate. Crystallization was performed from acetone/ether to obtain Compound 76 (41.2 mg, 60%).

Yield: 60%

Melting point: 148–151° C. (acetone/ether)

Optical purity: >99% ee [CHIRALCEL OD column (4.6× 250 mm), Daicel Chemical Industries, elution solvent: ethanol]

$^1$H NMR (270 MHz, $CDCl_3$) δ: 0.95 (t, 3H, J=7.3 Hz), 1.63–1.98 (m, 8H), 2.04–2.18 (m, 2H), 2.90 (dd, 1H, J=14.2, 7.6 Hz), 3.07 (dd, 1H, J=13.9, 4.3 Hz), 3.24 (quin, 1H, J=8.2 Hz), 4.03 (dd, 1H, J=11.8, 6.3 Hz), 4.05 (t, 2H, J=7.6 Hz), 4.15 (dd, 1H, J=11.9, 9.9 Hz), 4.60 (m, 1H), 6.77 (d, 2H, J=8.3 Hz), 7.03 (d, 2H, J=8.3 Hz), 8.62 (s, 1H)

IR ($CHCl_3$) 1716, 1682, 1581, 1558, 1540, 1385 $cm^{-1}$

EI-MS: m/e 393 ($M^+$)

Example 75

Compound 77

To a solution of 6-methylthio-3-propyl-8-(3-pyridyl)-7H-purin-2(3H)-one (15 mg, 50 mmol) obtained by a known method (Journal of Medicinal Chemistry, vol. 36, p. 2508, 1993) or in the same manner as Example 40 in chloroform or chloroform/methanol (4/1, 0.20 mL) was added a solution of (R)-phenylalaninol (0.50 mmol/L) in methanol (0.20 mL) and the mixture was heated at 80° C. with stirring. After the solvent was removed, the reaction mixture was stirred at 150° C. for 5 hours. To the reaction residue were added dichloromethane (2.0 mL), pyridine (two drops) and methanesulfonyl chloride (two drops), and the mixture was stirred at room temperature for 3 hours. The reaction solvent was evaporated, and to the residue were added water (1.0 mL) and ethyl acetate (1.0 mL). The mixture was passed through a diatomaceous earth column, the column was washed with ethyl acetate (6.0 mL), and then the eluates were concentrated. A solution of the residue in dichloromethane (1.0 mL) was applied to a solid phase extraction cartridge (SCX, 500 mg), and the cartridge was washed with dichloromethane (2.0 mL) and methanol (3.0 mL). Compound 77 was eluted with a 2 mol/L ammonia solution in methanol (3 mL) and the eluate was concentrated. The residue was purified by silica gel column chromatography to obtain Compound 77 (7.6 mg, 39%).

ESI-MS: m/e 387 ($M^+$+1)

Compounds 78 to 92 were obtained in the same manner as Example 75.

The aminoalcohols used in Examples 84 to 90 (Table 2) were prepared as follows. To a solution of diphenyliminoglycine (53.4 mg, 200 mmol) in N,N-dimethylformamide (0.8 mL) were added 2-tert-butylimino-2-diethylamino-1,3-dimethylperhydro-1,3,2-diazaphospholine polystyrene resin (<2.3 mmol base/g, 0.2 g) and a corresponding substituted benzyl halide (300 mmol), and the mixture was stirred overnight at room temperature. The reaction mixture was filtered and concentrated under reduced pressure. To the residue were added tetrahydrofuran (800 mL) and 1 mol/L hydrochloric acid (100 mL), the mixture was stirred at room temperature for 2 hours, and then the solvent was evaporated under reduced pressure. To the residue were added 50% ethanol/water (600 mL) and a solution of sodium borohydride (76 mg, 2 mmol) in 50% ethanol/water (2 mL), and the mixture was stirred at room temperature for two days. The solvent was removed under reduced pressure, to the resulting residue were added ethyl acetate (3 mL) and water (0.1 mL), and the mixture was passed through a diatomaceous earth column. Ethyl acetate was applied (3 mL×2), the resulting eluate was concentrated under reduced pressure, and the residue was treated in a solid phase extraction cartridge (SCX, 500 mg) to obtain a substituted phenylalaninol in an approximate yield of 82 to 100%.

TABLE 2

| Example | Substituted benzyl halide | Aminoalcohol |
|---|---|---|
| 84 | 4-tert-Butylbenzyl bromide | 2-Amino-3-(4-tert-butylphenyl)-1-propanol |
| 85 | 2-Phenylbenzyl bromide | 2-Amino-3-(2-biphenyl)-1-propanol |
| 86 | 3-Trifluoromethylbenzyl bromide | 2-Amino-3-(3-trifluoromethylphenyl)-1-propanol |
| 87 | 3-(2-Fluorophenoxy)benzyl bromide | 2-Amino-3-[3-(2-fluorophenoxy)phenyl]-1-propanol |
| 88 | 3-Phenoxybenzyl chloride | 2-Amino-3-(3-phenoxyphenyl)-1-propanol |
| 89 | 3-Trifluoromethoxybenzyl bromide | 2-Amino-3-(3-trifluoromethoxyphenyl)-1-propanol |
| 90 | 3,5-Bis(trifluoromethyl)benzyl bromide | 2-Amino-3-[3,5-bis(trifluoromethyl)phenyl]-1-propanol |

Example 76

Compound 78

EI-MS: m/e 386 (M$^+$)

Example 77

Compound 79

ESI-MS: m/e 406 (M$^+$+1)

Example 78

Compound 80

ESI-MS: m/e 430 (M$^+$+1)

Example 79

Compound 81

ESI-MS: m/e 387 (M$^+$+1)

Example 80

Compound 82

ESI-MS: m/e 388 (M$^+$+1)

Example 81

Compound 83

ESI-MS: m/e 392 (M$^+$+1)

Example 82

Compound 84

ESI-MS: m/e 350 (M$^+$+1)

Example 83

Compound 85

ESI-MS: m/e 412 (M$^+$+1)

Example 84

Compound 86

EI-MS: m/e 433 (M$^+$)

Example 85

Compound 87

EI-MS: m/e 453 (M$^+$)

Example 86

Compound 88

EI-MS: m/e 445 (M$^+$)

Example 87

Compound 89

EI-MS: m/e 487 (M$^+$)

Example 88

Compound 90

EI-MS: m/e 469 (M$^+$)

Example 89

Compound 91

EI-MS: m/e 461 (M$^+$)

Example 90

Compound 92

EI-MS: m/e 513 (M$^+$)

Example 91

Compound 93

Compound 93 was obtained from 2-amino-2-methyl-3-phenyl-1-propanol, which was obtained from α-methylphenylalanine by a known method, and Compound 6a in the same manner as Example 1.

Yield: 10%

Melting point: 130–135° C.

$^1$H-NMR (270 MHz, CDCl$_3$) δ: 0.94 (t, 3H, J=7.3 Hz), 1.42 (s, 3H), 1.45 (s, 3H), 1.68–1.85 (m, 8H), 2.10 (m, 2H), 3.21 (q, 1H, J=7.8 Hz), 3.81 (dd, 1H, J=11.9, 6.8 Hz), 3.88 (t, 1H, J=11.9 Hz), 4.00 (t, 2H, J=7.3 Hz), 4.41 (dd, 1H, J=9.5, 6.8 Hz), 7.16–7.38 (m, 5H)

IR (neat): 1695, 1651, 1495 cm$^{-1}$

EI-MS: m/e 391 (M$^+$)

Test Example 1

Acute Toxicity Test

A test compound was orally administered to dd male mice (body weight: 20±1 g, n=3). Mortality rate after seven days was measured to determine minimum lethal dose (MLD). As a result, MLD of Compound 16 was not less than 300 mg/kg (mice, po), which revealed safety of the medicament of the present invention.

Test Example 2

Insulin Secretion Enhancing Action in Cultured β-cell

The established pancreas β-cell, MIN6 cell, reported by Miyazaki et al. (Endocrinology, vol. 127, pp.126–131, 1990) exhibits insulin content and insulin secretion amount by stimulation with glucose similar to those of pancreas β-cells in living bodies, and well preserves characteristics of pancreas β-cells in living bodies from a viewpoint that it shows increase of insulin secretion in a glucose concentration-dependent manner (the above reference and Ishihara et al., Diabetologia, vol. 36, pp.1139–1145, 1993). Further, the insulin secretion of the MIN6 cell is enhanced in response to sulfonylurea agents such as glibenclamide, which are used as a medicament for treatment of diabetes (Beng et al., Cellular Signalling, vol. 5, pp.777–786, 1993).

Culture of the $MIN_6$ cells and insulin secretion test utilizing the $MIN_6$ cells were performed basically according to the methods described in literature (Ishihara et al., Diabetologia, vol. 36, pp.1139–1145, 1993). The effect of a compound on the insulin secretion in the presence of 14.5 mM glucose was determined by measuring insulin amounts in cell culture supernatants collected as follows. MIN6 cells cultured on a 24-well plate were washed twice by using 1 ml of Buffer A (119 mM sodium chloride, 4.74 mM potassium chloride, 2.54 mM calcium chloride, 1.19 mM magnesium sulfate, 1.19 mM potassium dihydrogenphosphate, 10 mM 2-[4-(2-hydroxyethyl)-1-piperazinyl]ethanesulfonic acid, 0.1% bovine serum albumin, pH 7.3) containing 2 mM glucose, and then were incubated in 1 ml of Buffer A containing 2 mM glucose at 37° C. for 45 minutes. After the incubation, the culture supernatant was changed to Buffer A (0.9 ml) containing a test compound at various concentrations and 2 mM glucose, and the cells were further incubated at 37° C. for 15 minutes. The MIN6 cells were stimulated with glucose by the addition of Buffer A (0.1 ml) containing 127 mM glucose to the culture (final glucose concentration: 14.5 mM). After the stimulation, the cells were further incubated at 37° C. for 45 minutes, and then the culture supernatant was collected.

Separately, the effect of a compound on the insulin secretion in the presence of 5 mM glucose was determined by measuring insulin amounts in cell culture supernatants collected as follows. MIN6 cells cultured on a 24-well plate were washed twice by using 1 ml of Buffer A containing 5 mM glucose, and then the culture supernatant was changed to Buffer A (0.9 ml) containing a test compound at various concentrations and 5 mM glucose. Then, the cells were incubated at 37° C. for 45 minutes (final glucose concentration: 5 mM), and the culture supernatant was collected.

After the culture supernatant was diluted with a phosphate buffer containing 1% bovine serum albumin, 0.1% Tween 20, 0.12% disodium ethylenediaminetetraacetate and 0.1% sodium azide, antibody-reactive insulin secreted in the culture supernatant was quantified by enzyme immunoassay or radio immunoassay. The insulin level was indicated as the amount of human insulin (ng/mL). The results are indicated as averages (avg) for 3 to 4 samples with standard error values (se).

TABLE 3

In the presence of 14.5 mM glucose

| Drug concentration ($\mu$M) | Compound No. | Amount of secreted insulin (ng/ml) | |
|---|---|---|---|
| | | avg | se |
| 0 | | 148.4 | 4.8 |
| 1.0 | 12 | 227.8 | 3.9 |
| 1.0 | 16 | 229.5 | 14.3 |
| 1.0 | 18 | 181.9 | 1.4 |
| 1.0 | 19 | 223.8 | 3.1 |
| 1.0 | 20 | 235.9 | 2.9 |
| 1.0 | 23 | 249.9 | 21.3 |
| 1.0 | 31 | 220.5 | 2.5 |
| 1.0 | 35 | 232.4 | 10.6 |
| 1.0 | 37 | 202.8 | 8.0 |
| 1.0 | 43 | 199.1 | 3.6 |
| 1.0 | 50 | 209.5 | 1.5 |
| 1.0 | 54 | 216.1 | 6.6 |
| 1.0 | 65 | 207.8 | 2.4 |
| 1.0 | AY4166 | 195.1 | 4.3 |
| 0.1 | Glibenclamide | 177.8 | 3.3 |

As shown in Table 3, it was revealed that the compounds of the present invention had insulin secretion enhancing action. Whilst, in the presence of glucose at a low concentration (5 mM), these compounds did not show marked secretion enhancing action even at a 10 times higher concentration. Glibenclamide (Pharmacotherapy, vol. 5, p.43, 1985) and AY-4166 (Yakuri To Rinsho [Pharmacology and Clinic], vol. 7, p.121, 1997) used as controls for comparison showed marked secretion enhancing action even at a low glucose concentration.

Test Example 3

Insulin Secretion Enhancing Action (Glucose-loading)

Wistar male rats (body weight: about 250 g) starved for 18 hours were anesthetized by intraperitoneal administration of sodium pentobarbital (50 mg/kg), and fixed at the dorsal position. Cannulas were inserted into the right common carotid artery for blood collection and the left femoral vein for administration of drug and glucose, respectively. To these rats were intravenously administered 500 U/kg of heparin to prevent blood coagulation. After about 0.2 ml of blood was collected, a drug was intravenously administered. Two minutes after the administration of the drug, blood was collected, and then glucose (10 mg/kg) was immediately administered intravenously. Then, blood was collected every 20 seconds for 2 minutes. Insulin concentration in plasma obtained by centrifugation was measured by radioimmunoassay. From an insulin concentration which increased after the glucose-loading, its area was calculated and considered the amount of secreted insulin. The insulin level was indicated as the amount of rat insulin (ng/mL). The results are shown in Table 4. As clearly shown in Table 4, the compounds of the present invention showed significant insulin secretion enhancing action after the glucose-loading (condition of hyperglycemia). On the other hand, they exhibited no secretion enhancing action at a low glucose concentration (normal condition).

TABLE 4

| | | Area of plasma insulin (ng · sec/ml) | | | | | |
|---|---|---|---|---|---|---|---|
| | | | Test compound-administered group | | | | |
| Test compound | n | Control Area | Dose (mg/kg, iv) | n | Area | % Ratio based on control | Significant difference |
| 16 | 6 | 7.02 ± 0.97 | 3 | 6 | 17.28 ± 1.35 | 246 ± 19 | *** |
| 19 | 6 | 4.61 ± 3.17 | 1 | 6 | 13.41 ± 1.95 | 291 ± 42 | * |
| 35 | 6 | 8.83 ± 2.17 | 1 | 6 | 15.69 ± 2.04 | 178 ± 23 | * |
| 23 | 6 | 5.19 ± 0.40 | 1 | 6 | 11.85 ± 2.58 | 228 ± 50 | * |
| 31 | 6 | 5.19 ± 0.40 | 1 | 6 | 9.00 ± 0.84 | 173 ± 16 | ** |

Significant difference: * P < 0.05,  P < 0.01, * P < 0.001 (student's t-test or Aspin-Welch test)

Test Example 4

Hyperglycemia Suppression Action after Glucose-loading

Wistar male rats (body weight: about 250 g) were anesthetized by intraperitoneal administration of sodium pentobarbital (50 mg/kg), and a cannula was fixed in the left common carotid artery. These rats were used for the experiment after starvation for 18 hours. A test compound was orally administered 1 hour before oral administration of glucose (2 g/kg). Jugular venous blood was collected before the administration of test compound, before the glucose-loading, 5, 10, 15, 30, 45 and 60 minutes after the glucose-loading, and plasma glucose concentration was measured (enzymatic method). The insulin level was indicated as amount of rat insulin (ng/mL). The results are shown in Table 5. As clearly shown in Table 5, the compound of the present invention showed hyperglycemia suppression action after glucose-loading (condition of hyperglycemia). On the other hand, they exhibited no hypoglycemic action under the normal condition.

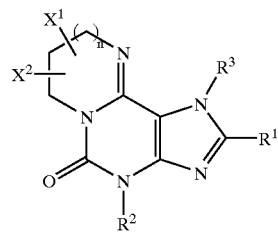

TABLE 5

| | | | Plasma glucose concentration (mg/dl) | | | | | | |
|---|---|---|---|---|---|---|---|---|---|
| Test compound | Dose (mg/kg, po) | n | −1 minute | 0 minute | 5 minutes | 10 minutes | 15 minutes | 30 minutes | 45 minutes | 60 minutes |
| Control | — | 5 | 114 ± 5.0 | 116 ± 7.8 | 152 ± 6.9 | 204 ± 10.7 | 231 ± 11.8 | 201 ± 12.5 | 189 ± 9.9 | 189 ± 3.2 |
| Compound 16 | 30 | 5 | 114 ± 4.5 | 102 ± 4.6 | 147 ± 5.7 | 183 ± 9.1 | 186 ± 8.7* | 167 ± 3.3* | 165 ± 4.8 | 178 ± 4.7 |

Significant difference: * P < 0.05 (student's t-test or Aspin-Welch test)

INDUSTRIAL APPLICABILITY

The medicament of the present invention has insulin secretion enhancing action and hypoglycemic action. In particular, the medicament is characterized to have superior hypoglycemic action under a hyperglycemic condition, whilst have no hypoglycemic action under a normal blood glucose level. Therefore, the medicament of the present invention is extremely useful to safely and effectively perform the therapeutic treatment of diabetes and the prophylactic and/or therapeutic treatment of complications of diabetes.

What is claimed is:

1. A method for therapeutic treatment of diabetes, which comprises administering to a mammal a therapeutically effective amount of a compound represented by the general formula (I), or a physiologically acceptable salt thereof:

(I)

wherein $R^1$ represents a hydrogen atom, a lower alkyl group, a substituted or unsubstituted aryl group, or a substituted or unsubstituted aromatic heterocyclic group;

$R^2$ represents a hydrogen atom, a lower alkyl group, a substituted or unsubstituted aralkyl group, a substituted or unsubstituted aryl group, or a substituted or unsubstituted aromatic heterocyclic group;

$R^3$ represents a hydrogen atom, a lower alkyl group, or a substituted or unsubstituted aralkyl group;

$X^1$ and $X^2$ independently represent a hydrogen atom, a lower alkyl group, a substituted or unsubstituted aralkyl group, or a substituted or unsubstituted aryl group; and the symbol "n" represents an integer of from 0 to 3.

2. The method according to claim 1, wherein $R^1$ represents a lower alkyl group, a substituted or unsubstituted aryl group, or a substituted or unsubstituted aromatic heterocyclic group;

$R^2$ represents a lower alkyl group or a substituted or unsubstituted aryl group;

$R^3$ represents a hydrogen atom or a substituted or unsubstituted aralkyl group;

$X^1$ represents a hydrogen atom, a lower alkyl group, or a substituted or unsubstituted aralkyl group;

$X^2$ represents a hydrogen atom; and the symbol "n" represents 0.

3. The method according to claim 1,
  wherein R¹ represents a n-propyl group, a n-butyl group, a cyclobutyl group, a cyclopentyl group, a cyclohexyl group, a cyclopropylmethyl group, a cyclopentylmethyl group, an isopropyl group, or a tert-butyl group;
  R² represents a n-propyl group or an ethyl group;
  R³ represents a hydrogen atom;
  X¹ represents a lower alkyl group or a substituted or unsubstituted aralkyl group;
  X² represents a hydrogen atom; and
  the symbol "n" represents 0.

4. The method according to claim 1, wherein the mammal is a human.

5. A method for therapeutic treatment of a complication of diabetes, which comprises administering to a mammal therapeutically effective amount of the compound represented by the general formula (I) or a physiologically acceptable salt thereof:

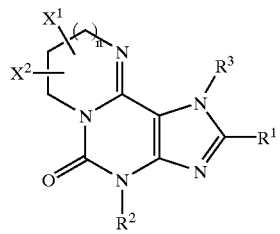

(I)

wherein R¹ represents a hydrogen atom, a lower alkyl group, a substituted or unsubstituted aryl group, or a substituted or unsubstituted aromatic heterocyclic group;
  R² represents a hydrogen atom, a lower alkyl group, a substituted or unsubstituted aralkyl group, a substituted or unsubstituted aryl group, or a substituted or unsubstituted aromatic heterocyclic group;
  R³ represents a hydrogen atom, a lower alkyl group, or a substituted or unsubstituted aralkyl group;
  X¹ and X² independently represent a hydrogen atom, a lower alkyl group, a substituted or unsubstituted aralkyl group, or a substituted or unsubstituted aryl group; and
  the symbol "n" represents an integer of from 0 to 3.

6. The method according to claim 5,
  wherein R¹ represents a lower alkyl group, a substituted or unsubstituted aryl group, or a substituted or unsubstituted aromatic heterocyclic group;
  R² represents a lower alkyl group or a substituted or unsubstituted aryl group;
  R³ represents a hydrogen atom or a substituted or unsubstituted aralkyl group;
  X¹ represents a hydrogen atom, a lower alkyl group, or a substituted or unsubstituted aralkyl group;
  X² represents a hydrogen atom; and
  the symbol "n" represents 0.

7. The method according to claim 5,
  wherein R¹ represents a n-propyl group, a n-butyl group, a cyclobutyl group, a cyclopentyl group, a cyclohexyl group, a cyclopropylmethyl group, a cyclopentylmethyl group, an isopropyl group, or a tert-butyl group;
  R² represents a n-propyl group or an ethyl group;
  R³ represents a hydrogen atom;
  X¹ represents a lower alkyl group or a substituted or unsubstituted aralkyl group;
  X² represents a hydrogen atom; and
  the symbol "n" represents 0.

8. The method according to claim 5, wherein the mammal is a human.

9. A method for lowering blood sugar level, which comprises administering to a mammal a therapeutically effective amount of the compound represented by the general formula (I) or a physiologically acceptable salt thereof:

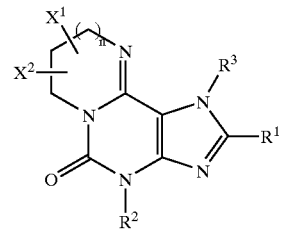

(I)

wherein R¹ represents a hydrogen atom, a lower alkyl group, a substituted or unsubstituted aryl group, or a substituted or unsubstituted aromatic heterocyclic group;
  R² represents a hydrogen atom, a lower alkyl group, a substituted or unsubstituted aralkyl group, a substituted or unsubstituted aryl group, or a substituted or unsubstituted aromatic heterocyclic group;
  R³ represents a hydrogen atom, a lower alkyl group, or a substituted or unsubstituted aralkyl group;
  X¹ and X² independently represent a hydrogen atom, a lower alkyl group, a substituted or unsubstituted aralkyl group, or a substituted or unsubstituted aryl group; and
  the symbol "n" represents an integer of from 0 to 3.

10. The method according to claim 9,
  wherein R¹ represents a lower alkyl group, a substituted or unsubstituted aryl group, or a substituted or unsubstituted aromatic heterocyclic group;
  R² represents a lower alkyl group or a substituted or unsubstituted aryl group;
  R³ represents a hydrogen atom or a substituted or unsubstituted aralkyl group;
  X¹ represents a hydrogen atom, a lower alkyl group, or a substituted or unsubstituted aralkyl group;
  X² represents a hydrogen atom; and
  the symbol "n" represents 0.

11. The method according to claim 9,
  wherein R¹ represents a n-propyl group, a n-butyl group, a cyclobutyl group, a cyclopentyl group, a cyclohexyl group, a cyclopropylmethyl group, a cyclopentylmethyl group, an isopropyl group, or a tert-butyl group;
  R² represents a n-propyl group or an ethyl group;
  R³ represents a hydrogen atom;
  X¹ represents a lower alkyl group or a substituted or unsubstituted aralkyl group;
  X² represents a hydrogen atom; and
  the symbol "n" represents 0.

12. The method according to claim 9, wherein the mammal is a human.

13. A method for enhancing insulin secretion, which comprises administering to a mammal a therapeutically effective amount of the compound represented by the general formula (I) or a physiologically acceptable salt thereof:

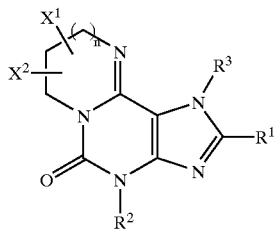

wherein $R^1$ represents a hydrogen atom, a lower alkyl group, a substituted or unsubstituted aryl group, or a substituted or unsubstituted aromatic heterocyclic group;
$R^2$ represents a hydrogen atom, a lower alkyl group, a substituted or unsubstituted aralkyl group, a substituted or unsubstituted aryl group, or a substituted or unsubstituted aromatic heterocyclic group;
$R^3$ represents a hydrogen atom, a lower alkyl group, or a substituted or unsubstituted aralkyl group;
$X^1$ and $X^2$ independently represent a hydrogen atom, a lower alkyl group, a substituted or unsubstituted aralkyl group, or a substituted or unsubstituted aryl group; and
the symbol "n" represents an integer of from 0 to 3.

14. The method according to claim 13,
wherein $R^1$ represents a lower alkyl group, a substituted or unsubstituted aryl group, or a substituted or unsubstituted aromatic heterocyclic group;
$R^2$ represents a lower alkyl group or a substituted or unsubstituted aryl group;
$R^3$ represents a hydrogen atom or a substituted or unsubstituted aralkyl group;
$X^1$ represents a hydrogen atom, a lower alkyl group, or a substituted or unsubstituted aralkyl group;
$X^2$ represents a hydrogen atom; and
the symbol "n" represents 0.

15. The method according to claim 13,
wherein $R^1$ represents a n-propyl group, a n-butyl group, a cyclobutyl group, a cyclopentyl group, a cyclohexyl group, a cyclopropylmethyl group, a cyclopentylmethyl group, an isopropyl group, or a tert-butyl group;
$R^2$ represents a n-propyl group or an ethyl group;
$R^3$ represents a hydrogen atom;
$X^1$ represents a lower alkyl group or a substituted or unsubstituted aralkyl group;
$X^2$ represents a hydrogen atom; and
the symbol "n" represents 0.

16. The method according to claim 13, wherein the mammal is a human.

* * * * *